US007479483B2

(12) United States Patent
Ponzoni et al.

(10) Patent No.: US 7,479,483 B2
(45) Date of Patent: Jan. 20, 2009

(54) TUMOR-TARGETED DRUG DELIVERY SYSTEMS AND USES THEREOF

(75) Inventors: Mirco Ponzoni, Genoa (IT); Angelo Corti, Bergamo (IT); Theresa M. Allen, Edmonton (CA)

(73) Assignees: G. Gaslini Children's Hospital (IT); Fondazione Centro San Raffaele del Monte (IT); University of Alberta (CA)

( * ) Notice: Subject to any disclaimer, the term of this patent is extended or adjusted under 35 U.S.C. 154(b) by 231 days.

(21) Appl. No.: 10/853,895

(22) Filed: May 26, 2004

(65) Prior Publication Data

US 2004/0258747 A1 Dec. 23, 2004

(30) Foreign Application Priority Data

May 29, 2003 (GB) ................................. 0312309.8

(51) Int. Cl.
*A61K 38/00* (2006.01)
(52) U.S. Cl. .............................. 514/12; 514/12; 514/13; 514/14; 514/15; 514/16
(58) Field of Classification Search .................. 514/12, 514/13, 14, 15, 16, 17
See application file for complete search history.

(56) References Cited

U.S. PATENT DOCUMENTS

| | | | |
|---|---|---|---|
| 5,622,699 | A | 4/1997 | Ruoslahti et al. |
| 6,056,973 | A | 5/2000 | Allen et al. |
| 6,068,829 | A | 5/2000 | Ruoslahti et al. |
| 6,180,084 | B1 | 1/2001 | Ruoslahti et al. |
| 6,296,832 | B1 | 10/2001 | Ruoslahti et al. |
| 6,306,365 | B1 | 10/2001 | Ruoslahti et al. |
| 6,316,024 | B1 | 11/2001 | Allen et al. |
| 6,491,894 | B1 * | 12/2002 | Ruoslahti et al. ............. 424/9.1 |
| 6,576,239 | B1 | 6/2003 | Ruoslahti et al. |
| 6,743,892 | B1 | 6/2004 | Ruoslahti et al. |
| 7,109,303 | B2 * | 9/2006 | Corti ....................... 530/387.3 |
| 2001/0038851 | A1 * | 11/2001 | Allen et al. .................. 424/450 |
| 2003/0157055 | A1 | 8/2003 | Corti |
| 2003/0157056 | A1 | 8/2003 | Corti |
| 2004/0018171 | A1 | 1/2004 | Corti |
| 2004/0058365 | A1 | 3/2004 | Panzer et al. |
| 2004/0166500 | A1 | 8/2004 | Panzer et al. |

FOREIGN PATENT DOCUMENTS

| | | |
|---|---|---|
| WO | WO 98/10795 A3 | 3/1998 |
| WO | WO 99/13329 | 3/1999 |
| WO | WO 01/61017 A | 8/2001 |
| WO | WO 200161017 A2 * | 8/2001 |
| WO | WO 02/079473 A | 10/2002 |

OTHER PUBLICATIONS

Pastorino et al. (Cancer Research 2003; 63: 7400-7409, IDS).*
McLaughlin et al. (Blood 2001; 98: 3332-3339).*
Fabio et al., "Doxorubicin-loaded fab' fragments of anti-disialoganglioside immunoliposomes selectively inhibit the growth and dissemination of human neuroblastoma in nude mice," Database Biosis, Biosciences Information Service, Philadelphia, PA, Jan. 1, 2003 Accession No. PREV200300074941.
Fabio et al., "Vascular damage and anti-angiogenic effects of tumor vessel-targeted liposomal chemotherapy," Database Biosis Biosciences Information Service, Philadelphia, PA, Nov. 1, 2003, Database Biosis Accession No. PREV200300570034.
Yvette et al., "A doxorabicin-CNGRC-peptide conjugate with prodrug properties," Database Biosis Biosciences Information Service, Philadelphia, PA, Mar. 1, 2002, Database Biosis Accession No. PREV200200296740.
Arap W. et al. Cancer treatment by targeted drug delivery to tumor vasculature in a mouse model. Science. Jan. 16, 1998;279(5349):377-80.
Colombo G. et al. Structure-activity relationships of linear and cyclic peptides containing the NGR tumor-homing motif. J Biol Chem. Dec. 6, 2002;277(49):47891-7.
Cumis F. et al. Improving chemotherapeutic drug penetration in tumors by vascular targeting and barrier alteration. J Clin Invest. Aug. 2002;110(4):475-82.
Cumis F. et al. Differential binding of drugs containing the NGR motif to CD13 isoforms in tumor vessels, epithelia, and myeloid cells. Cancer Res. Feb. 1, 2002;62(3):867-74.
Ellerby H.M. et al. Anti-cancer activity of targeted pro-apoptotic peptides. Nat Med. Sep. 1999;5(9):1032-8.

(Continued)

*Primary Examiner*—Brandon J Fetterolf
(74) *Attorney, Agent, or Firm*—Clark & Elbing LLP

(57) ABSTRACT

The present invention relates to targeted delivery systems for delivering therapeutic agents to tumor. The invention further relates to methods of delivering a therapeutic agent to a tumor for the prevention and treatment of cancer by killing tumor cells and tumor-associated endothelial cells. In particular, the present invention provides a tumor-targeted drug delivery system comprising a NGR-containing molecule linked to a delivery vehicle encapsulating a therapeutic agent, preferably a drug, such as a cytotoxic agent or a chemotherapeutic agent. Specifically, the delivery systems of the present invention are capable of delivering an increased amount of therapeutic agent to a tumor as compared to other delivery systems. In particular, the delivery systems of the present invention are capable of accumulating a higher amount of therapeutic agent in a tumor, or in the vicinity of a tumor cell or tumor-supporting cell, resulting in exposure of the tumor cell and tumor-associated endothelial cell to therapeutic levels of the agent for a longer period of time as compared to other delivery systems. The present invention also describes pharmaceutical compositions comprising the delivery systems of the present invention. The present invention further relates to a tumor treatment comprising an increased amount of therapeutic agent delivered by the system of the present invention as compared to other delivery systems. The delivery systems and pharmaceutical compositions can be administered to a subject, preferably a human, alone or in combination, sequentially or simultaneously, with other prophylactic or therapeutic agents and/or anti-cancer treatments.

25 Claims, 11 Drawing Sheets

OTHER PUBLICATIONS

Figure 1F:
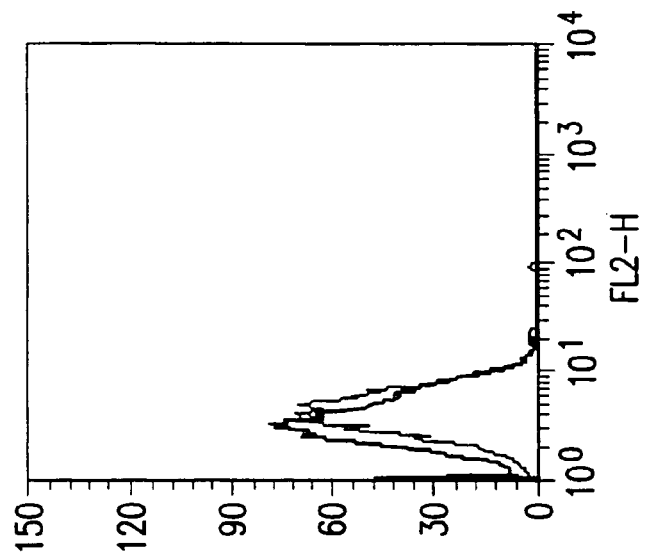

Huang X. et al. Tumor infarction in mice by antibody-directed targeteing of tissue factor to tumor vasculature. Science Jan. 24, 1997; 275:547-50.

Jain R.K. Delivery of molecular medicine to solid tumors. Science. Feb. 23, 1996;271(5252):1079-80.

Muggia F. et al. Phase III data on Caelyx in ovarian cancer. Eur J Cancer. Dec. 2001;37 Suppl 9:S15-8.

Pastorino F. et al. Vascular damage and anti-angiogenic effects of tumor vessel-targeted liposomal chemotherapy. Cancer Res. Nov. 1, 2003;63(21):7400-9.

Pastorino F. et al. Doxorubicin-loaded Fab' fragments of anti-disialoganglioside immunoliposomes selectively inhibit the growth and dissernination of human neuroblastoma in nude mice. Cancer Res. Jan. 1, 2003;63(1):86-92.

Wu G. et al. Receptor-mediated in vitro gene transformation by a soluble DNA carrier system. J Biol Chem Apr. 5, 1987;262(10):4429-32.

Van Hensbergen et al., "A doxorubicin-CNGRC-peptide conjugate with prodrug properties," *Biochem. Pharmacol.* 5: 897-908 (2002).

International Search Report for International Application No. PCT/EP2004/005677 filed May 26, 2004, International Search Report published Apr. 21, 2005.

\* cited by examiner

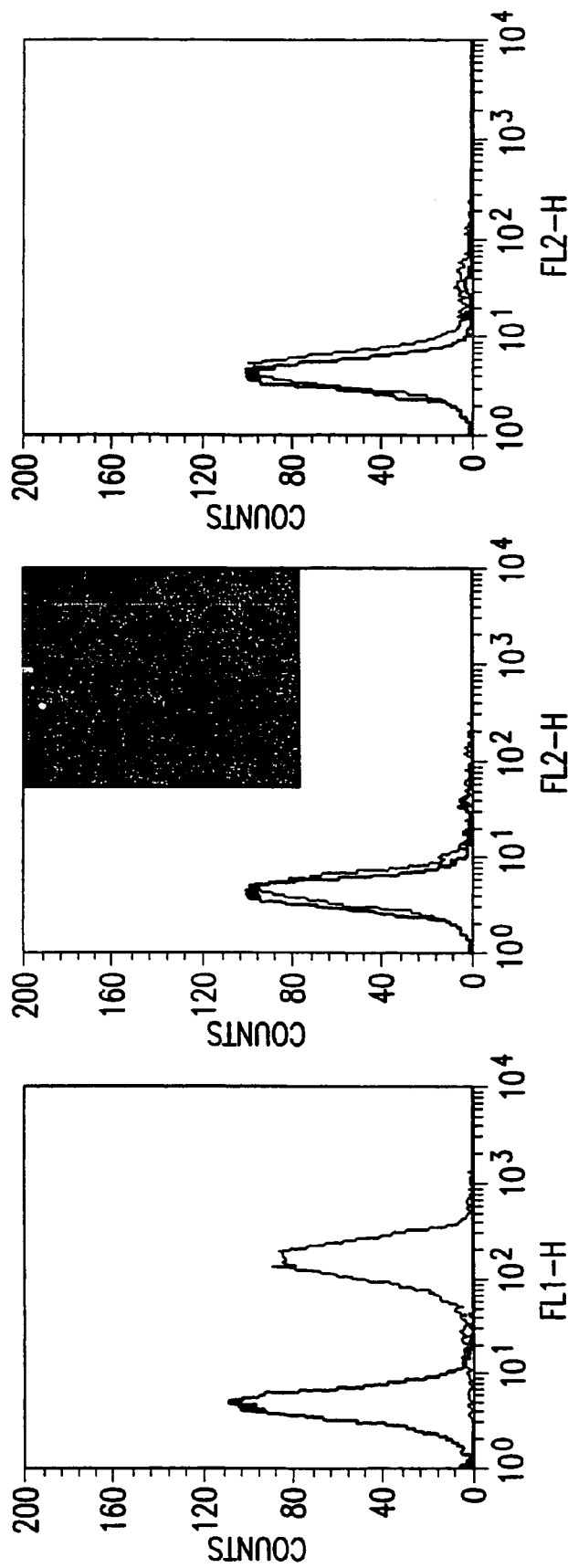

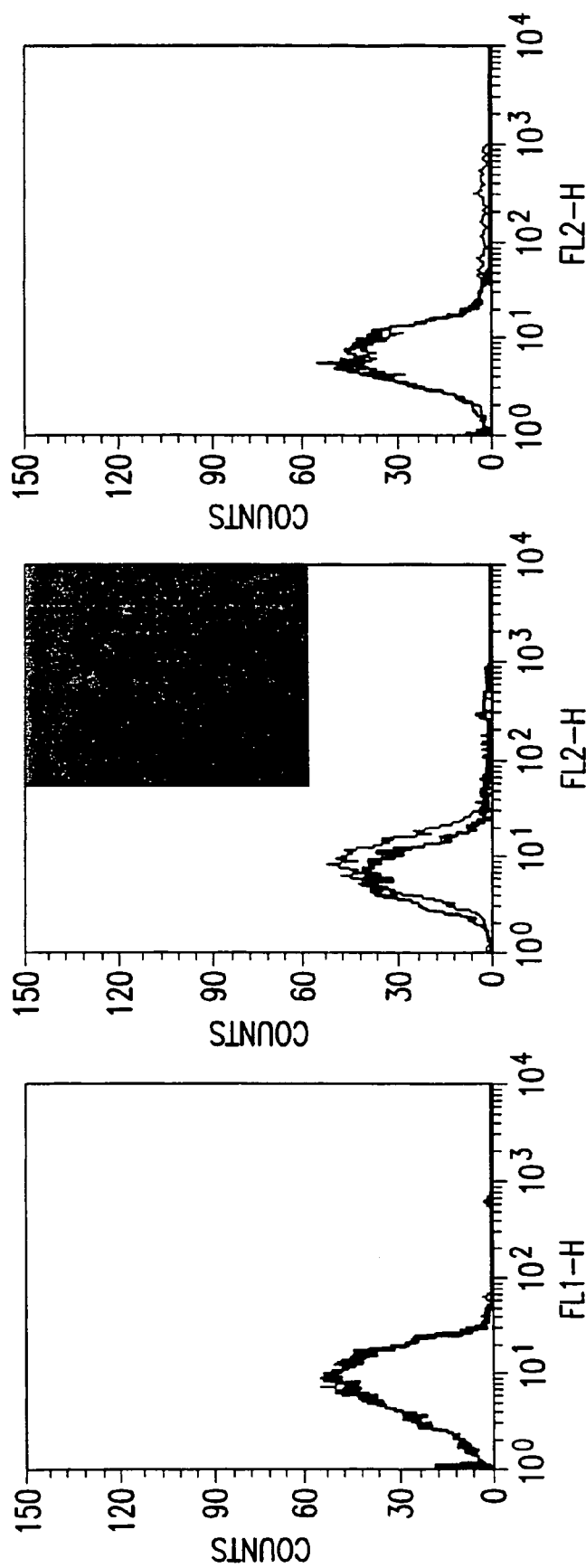

  
FIG.4B  FIG.4C  FIG.4D
  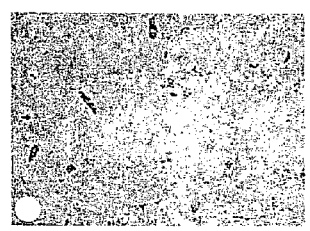
FIG.4E  FIG.4F  FIG.4G
 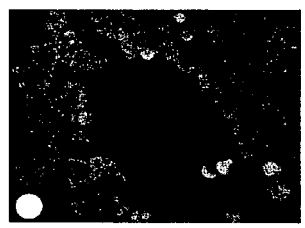 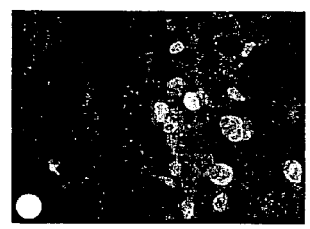
FIG.4H  FIG.4I  FIG.4J
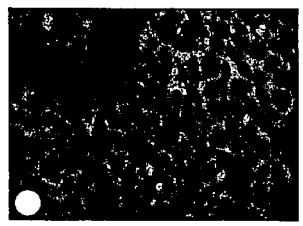 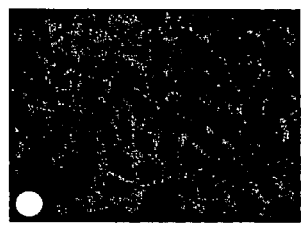 
FIG. 4K  FIG. 4L  FIG. 4M

TUMOR-TARGETED DRUG DELIVERY SYSTEMS AND USES THEREOF The present application claims priority to United Kingdom Patent Application No. 0312309.8, filed May 29, 2003, which is incorporated herein by reference in its entirety.

1. Field of the Invention

The present invention relates to targeted delivery systems for delivering therapeutic agents to tumors, in particular to tumor cells and tumor-associated endothelial cells. The invention further relates to methods of delivering a therapeutic agent to tumor cells and tumor-associated endothelial cells for the prevention and treatment of cancer by killing tumor cells and tumor-associated endothelial cells. In particular, the present invention provides a tumor-targeted drug delivery system comprising a NGR-containing molecule linked to a delivery vehicle encapsulating a therapeutic agent, preferably a drug, such as a cytotoxic agent or a chemotherapeutic agent. Specifically, the delivery systems of the present invention are capable of delivering an increased amount of therapeutics to tumor cells and tumor-associated endothelial cells as compared to other delivery systems. In particular, the delivery systems of the present invention are capable of accumulating a higher amount of therapeutic agent in tumor cells, or in cells that contribute to tumor cell viability (e.g. vascular endothelial cells), and of leading to exposure of these cells to therapeutic levels of the agent for a longer period of time as compared to other delivery systems. The present invention also describes pharmaceutical compositions and tumor cells comprising the delivery systems of the present invention. The present invention further relates to a tumor cell or a cell that contributes to tumor cell viability comprising an increased amount of therapeutic agent delivered by the system of the present invention as compared to other delivery systems. The delivery systems and pharmaceutical compositions can be administered to a subject, preferably a human, alone or in combination, sequentially or simultaneously, with other prophylactic or therapeutic agents and/or anti-cancer treatments.

2. Background of the Invention

Most chemotherapeutic drugs act on both normal as well as cancerous tissues. As such, one of the challenges in treating cancerous tumors with chemotherapy is maximizing the killing of cancer cells while minimizing the harming of healthy tissue. Depending on the administration route (e.g., intravenous) and nature of the drug (e.g., its physical and pharmacokinetic properties), oftentimes only a small fraction of the dose reaches the target cells; the remaining amount of drug acts on other tissues or is rapidly eliminated.

To improve delivery efficiency and reduce toxicity to non-target cells, various strategies have been used to deliver drugs to specific sites in the human body. For example, the use of a monoclonal antibody conjugated to a toxin has been reported in cancer treatment. The antibody provides selectivity for the target, but there still remains the problem of interaction with non-target cells during passage to the intended site of action.

The alternative approach of encapsulating toxins in liposomes has also been actively researched. Liposomes are structures consisting essentially of a membrane bilayer composed of lipids of biological or synthetic origin such as phospholipids, sphingolipids, glycosphingolipids, ceramides or cholesterol. Liposomes can encapsulate large quantities of drug molecules either within their aqueous interiors or dissolved into the hydrocarbon regions of their bilayers. Liposomes can also protect their contents from rapid filtration by the kidneys and from degradation by metabolism, thus enhancing the drug's residence time in the body. Once taken up by a target cell (e.g. by ligand-mediated endocytosis), liposomes may also facilitate the cytoplasmic delivery of encapsulated drug molecules by fusing with the endosomal membrane. However, the clinical utility of liposomes in targeting drug delivery has been severely limited by: (1) the rapid clearance by phagocytic cells of the reticuloendothelial system (RES), (2) the lack of specific tumor targeting, and (3) the premature or inappropriate release of the drug.

Thus, there is a need for a drug delivery system that is capable of delivering an increased amount of a therapeutic agent to tumor cells and to cells that support tumor cell viability and that these cells will be exposed to therapeutic levels of the agent over an extended period of time. There is also a need for delivery vehicles that have a sufficient survival time in vivo to effectively deliver a therapeutic agent to the desired cells. There is a further need for a drug delivery system having generic applicability to a wide range of cancers. An additional need is a drug delivery system that minimizes the cytotoxicity of the drug in normal tissue while retaining its effectiveness against neoplastic tissue. This invention satisfies these and other needs.

3. SUMMARY OF THE INVENTION

The present invention is based, in part, on the observations by the present inventors that liposomes operably linked to NGR-containing molecules can improve cancer treatment by exposing tumors to therapeutic levels of a therapeutic agent for an extended period of time as compared to other delivery systems. Without being bound by any theory, the inventors believe that this is accomplished by the dual mechanisms of ligand-mediated targeting and passive targeting. On one hand, the mechanism for the passive targeting effect stems from increased localization of the liposomal anti-cancer drugs (in a ligand-independent manner) to the tumor interstitial space due to increased permeability of the tumor vasculature, i.e., the so-called EPR (enhanced permeability and retention) effect, followed by sustained release of the drug and uptake of the released drug into the tumor cells and direct tumor cell kill. On the other hand, the mechanism for the indirect killing of the tumor cells results from the binding of ligand-targeted liposomal anticancer drugs to the cells that support tumor viability (e.g., tumor vascular endothelial cells). The targeted liposomal drugs are internalized into these tumor-supporting cells where they release their cytotoxic content resulting in the killing of the tumor-supporting cells. Indirect tumor cell kill is accomplished by depriving the tumor cells of substances essential for their viability and growth (e.g., oxygen and nutrients). It is speculated that the combined ligand-mediated and passive targeting effects reduce the side-effects of chemotherapeutic drugs on non-cancerous cells and result either in improved therapeutic efficacies or in efficacies that are more efficient than those found with conventional therapy for solid tumors. As a result, the liposomal delivery systems of the present invention are capable of delivering an increased amount of therapeutic agent to the tumor and of prolonging the exposure of the tumor to therapeutic levels of the agent.

In certain embodiments, the present invention relates to a tumor-targeted drug delivery system comprising a plurality of NGR-containing peptides linked to an encapsulating delivery vehicle comprising a drug, preferably a cytotoxic agent, a chemotherapeutic drug, an anti-angiogenic drug, or an anti-inflammatory drug. The tumor-targeted drug delivery system can directly target cells that express a NGR receptor, preferably tumor vascular endothelial cells, and passively target neighboring tumor cells that either express or lack the NGR receptor.

The present invention provides methods of delivering an increased amount of therapeutic agent to tumors. In specific embodiments, the increase in exposure level of the tumor to the therapeutic agent is 0.5-2 folds, 2-5 folds, 5-10 folds, 10-15 folds, 15-20 folds, 20-30 folds, or 30-40 folds higher over a period of time as compared to that of using other delivery systems. In specific embodiments, the tumor is exposed to increased levels of therapeutic agent by over 2-10%, 10-20%, 20-30% 30-40%, 40-50%, 50-60%, 60-70%, 70-80%, 80-90%, or 90-99% over a period of at least 2-5 hours, 5-10 hours, 10-12 hours, 12-24 hours, 24-36 hours, 36-48 hours, 3-5 days, 5-7 days, or 1-3 weeks as compared to that of using other delivery systems.

The present invention provides methods for the prevention and treatment of cancer comprising administering the delivery system of the present invention to a subject in which an increased amount of therapeutic agent is delivered to a tumor as compared to other delivery systems. In specific embodiments, the increase in the time of exposure of a tumor to the therapeutic agent is 0.5-2 fold, 2-5 fold, 5-10 fold, 10-15 fold, 15-20 fold, 20-30 fold, or 30-40 fold higher as compared to that of other delivery systems. In specific embodiments, the tumor is exposed to increased levels of therapeutic agents by over 2-10%, 10-20%, 20-30%, 30-40%, 40-50%, 50-60%, 60-70%, 70-80%, 80-90%, or 90-99% over a period of at least 2-5 hours, 5-10 hours, 10-12 hours, 12-24 hours, 24-36 hours, 36-48 hours, 3-5 days, 5-7 days, or 1-3 weeks as compared to other delivery systems. In other specific embodiments, the methods of the present invention further comprises administration of other therapies or therapeutic agents simultaneously or sequentially.

In one embodiment, the encapsulating delivery vehicle can be a liposome, micelle, lipidic micelle, microsphere, nanosphere, chambered microdevice, emulsion, lipid disc, polymer, cell, viral particle or virus. Preferably, the delivery vehicle is a liposome.

In a specific embodiment, the plurality of NGR-containing peptides are operably linked to the encapsulating delivery vehicle through a linking agent.

The present invention also relates to pharmaceutical compositions comprising one or more delivery systems of the present invention. Such pharmaceutical compositions can further include additional carriers and biological agents.

Methods for making and using the delivery system, pharmaceutical compositions, and disease targets are also described.

In one embodiment, the invention is directed to methods of preventing or treating a subject diagnosed or suspected of having a cancer, of all types, by the administration of an effective amount of one or more delivery systems or pharmaceutical compositions to the subject. In preferred embodiments, the amount of therapeutic agent that is delivered to a tumor is at least 0.5-2 folds, 2-5 folds, 5-10 folds, 10-15 folds, 15-20 folds, 20-30 folds, or 30-40 folds higher over a period of time as compared to that of using other delivery systems. In other embodiments, the amount of therapeutic agent that is delivered to the tumor is above the minimum therapeutic range required for the desired therapeutic activity. In specific embodiments, the tumor is exposed to over 2-10%, 10-20%, 20-30%, 30-40%, 40-50%, 50-60%, 60-70%, 70-80%, 80-90%, or 90-99% of the theraputic agent over a period of at least 2-5 hours, 5-10 hours, 10-12 hours, 12-24 hours, 24-36 hours, 36-48 hours, 3-5 days, 5-7 days, or 1-3 weeks as compared to other delivery systems. In a preferred embodiment, the survival of the cancer patient is prolonged. In another preferred embodiment, the growth of the tumor in the cancer patient is reduced. In certain embodiments, the growth of the tumor cells is reduced by at least 2-10%, 10-20%, 20-30%, 30-40%, 40-50%, 50-60%, 60-70%, 70-80%, 80-90%, 90-100% as compared to other delivery systems.

The invention further relates to combination therapies for treating cancer in a subject by administering to said subject a therapeutically or prophylactically effective amount of one or more delivery systems and/or pharmaceutical compositions, sequentially or simultaneously, with surgery, standard and experimental chemotherapies, hormonal therapies, biological therapies, immunotherapies, radiation therapies, embolization, and/or chemoembolization therapies for the treatment or prevention of cancer.

In another embodiment, the delivery system is also useful for preventing or treating a disease or condition associated with damaged or defective cells that express an NGR receptor.

3.1 Definition

As used herein, the term "NGR-containing molecule" includes a peptide, polypeptide, or protein modified peptide polypeptide, protein or derivatives thereof, comprising an amino acid sequence of at least 3 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino acid residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, at least contiguous 350 amino acid residues. In other preferred embodiments, NGR-containing molecule may be at most 300 daltons, 300-500 daltons, 500-1,000 daltons, 1,000-5,000 daltons, 5,000-200,000 daltons, 200,000-500,000 daltons in size.

As used herein, the term "tumor" or "tumors" comprises tumor cells and tumor stromal cells. Tumor stromal cells include tumor-supporting cells such as tumor vasculature endothelial cells, pericytes, tumor-associated macrophages and other tumor-associated tumor inflammatory cells.

As used herein, the terms "parenteral drug delivery", "parenteral therapeutic agent delivery" or "parenteral delivery" refer to delivery of therapeutic agents via routes other than enteral, where enteral includes only oral and rectal (into the gastrointestinal tract). The term parenteral includes, for example, intravenous, subcutaneous, intramuscular, intrathecal, intracerebral, intracerebral, and inhalation.

As used herein, the term "in combination" refers to the use of more than one prophylactic and/or therapeutic agents.

As used herein, the terms "manage," "managing" and "management" refer to the beneficial effects that a subject derives from the administration of a prophylactic or therapeutic agent, which do not result in a cure but the prevention of further progression or worsening of the disease or disorder.

As used herein, the terms "prevent," "preventing" and "prevention" refer to the deterrence of onset of the disease or disorder in a subject resulting from the administration of a prophylactic or therapeutic agent.

As used herein, the terms "prophylactic agent" and "prophylactic agents" refer to any agent(s) that can be used in the prevention of a disease or disorder.

As used herein, the term "prophylactically effective amount" refers to that amount of the prophylactic agent sufficient to prevent the onset of the disease or disorder.

As used herein, the term "side effects" encompasses unwanted and adverse effects of a prophylactic or therapeutic agent. Adverse effects are always unwanted, but unwanted effects are not necessarily adverse. An adverse effect from a prophylactic or therapeutic agent might be harmful or uncomfortable or risky. Side effects include, but are not limited to, gastrointestinal toxicity, early and late-forming diarrhea and flatulence, nausea, vomiting, anorexia, leukopenia, anemia, neutropenia, asthenia, abdominal cramping, fever, pain, loss of body weight, dehydration, alopecia, dyspnea, insomnia, dizziness, mucositis, xerostomia, and kidney failure, constipation, nerve and muscle effects, temporary or permanent damage to the heart, kidneys and bladder, flu-like symptoms, fluid retention, infertility problems, fatigue, dry mouth, loss of appetite, hair loss, rashes or swellings at the site of administration, flu-like symptoms such as fever, chills and fatigue, digestive tract problems, allergic reactions, depression, loss of appetite, eye problems, headache, and weight fluctuation. Additional undesired effects typically experienced by patients are numerous and known in the art (see e.g., Physicians' Desk Reference (56th ed., 2002)).

As used herein, the terms "subject" and "patient" are used interchangeably. As used herein, a subject is preferably a mammal such as a non-primate (e.g., cows, pigs, horses, cats, dogs, rats etc.) and a primate (e.g., monkey and human), most preferably a human.

As used herein, the terms "treat," "treating" and "treatment" refer to the amelioration or elimination of symptoms or recovering from the disease or disorder in a subject resulting from the administration of a therapeutic agent.

As used herein, the terms "therapeutic agent" and "therapeutic agents" refer to any agent(s) that can be used in the treatment of a disease or disorder.

As used herein, the term "therapeutically effective amount" refers to that amount of the therapeutic agent sufficient to reduce or minimize the symptoms of the disease or disorder and, preferably, result in the reduction in growth of tumor or cancer and/or survival of the subject.

As used herein, the terms "therapies" and "therapy" can refer to any protocol(s), method(s) and or agent(s) that can be used in the prevention, treatment, or management of diseases or disorder. In certain embodiments, the terms "therapy" and "therapies" refer to cancer chemotherapy, radiation therapy, hormonal therapy, biological therapy, and/or other therapies useful for the treatment of cancer, infectious diseases, autoimmune and inflammatory diseases known to a physician skilled in the art.

As used herein, the term "analog" refers to any member of a series of peptides having a common biological activity, including antigenicity/immunogenicity and antiangiogenic activity, and/or structural domain and having sufficient amino acid identity as defined herein.

As used herein, the term "variant" refers either to a naturally occurring allelic variation of a given peptide or a recombinantly prepared variation of a given peptide or protein in which one or more amino acid residues have been modified by amino acid substitution (preferably conservative), addition, or deletion.

As used herein, the term "derivative" refers to a variation of given amino acid, peptide or protein that are otherwise modified, i.e., by covalent attachment of any type of molecule, preferably having bioactivity, to the amino acid, peptide or protein, derivatives of an amino acid, including non-naturally occurring amino acids.

As used herein, the term "fragment" includes a peptide, polypeptide, or protein modified peptide polypeptide, protein or derivatives thereof, comprising an amino acid sequence of at least 3 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino acid residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, at least contiguous 350 amino acid residues.

When referring to the administration of therapeutic agents or system of the present invention, the term "simultaneously" or "simultaneous" refers to the administration of two or more therapies or therapeutic agents within the same 24 hours period, whereas "sequentially" and "subsequently" are intended to mean that the therapeutic agents are separated by more than 24 hours, such as separated by days, weeks, months, years, depending on the effects of a particular therapeutic agent. In one preferred embodiment, "sequential" or "subsequent" refers to dosages that are separated by one day to six weeks.

4. FIGURES

Figure 1E:
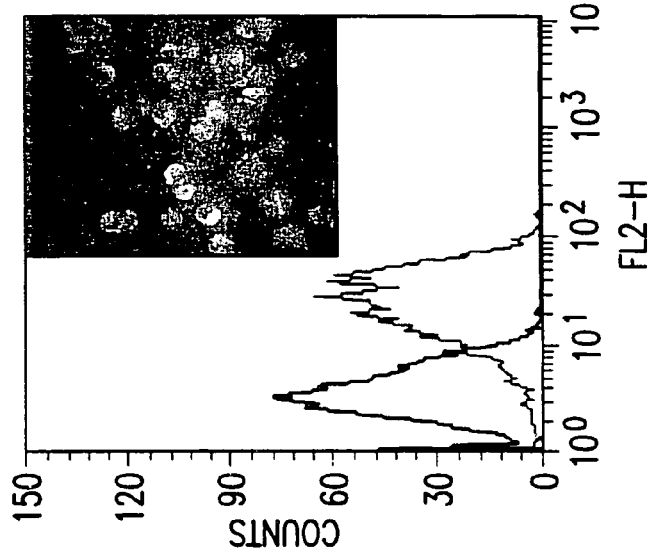

FIGS 1a-1i. Cellular association of NGR targeted liposomes were analyzed by flow cytometry in THP-1 cells (FIGS. 1a-1c), KS1767 cells (FIGS. 1d-1f), and SH-SY5Y cells (FIGS. 1g-1i). Cells were incubated with WM 15 monoclonal antibody (FIGS. 1a, 1d, 1g), NGR-SL[DXR] (FIGS. 1b, 1e, 1h), or ARA-SL[DXR] (FIGS. 1c, 1f, 1i). After washing, cells treated with WM 15 were incubated with a goat anti-mouse-FITC secondary antibody and then analyzed by FACS (FIGS. 1a, 1d, 1g: thin lines, WM15; bold lines, none). Cells treated with liposomal DXR were washed and directly enumerated by FACS (FIGS. 1b, 1c, 1e, 1f, 1h, 1i: thin lines, targeted liposomes; bold lines, non-targeted liposomes). In the insets of FIGS. 1b, 1e and 1h, cells were evaluated for DXR fluorescence by fluorescence microscopy.

FIGS. 2a-2h. Orthotopic neuroblastoma xenograft model in SCID mice. Adrenal gland tumors (arrows) in mice that were injected orthotopically with SH-SY5Y cells at 14 (FIG. 2a) and 21 (FIG. 2b) days before sacrifice. Representative right adrenal gland (FIG. 2c) and liver (FIG. 2d) samples at three and four weeks after injection of NB cells, respectively. Histological (H&E) analysis of representative ovary (FIG. 2e), kidney (FIG. 2f), liver (FIG. 2g), and lung (FIG. 2h) samples. Forty days after cell injection, animals were sacrificed, the organs were removed, fixed, paraffin embedded, sectioned at 5 μm and mined with H&E. Arrows indicate metastatic tumor invasion in the lung. Arrowheads show the normal ovaric follicular structure surrounded by tumor NB cells. Magnification ×10 (insets, ×63).

Figure 3A:
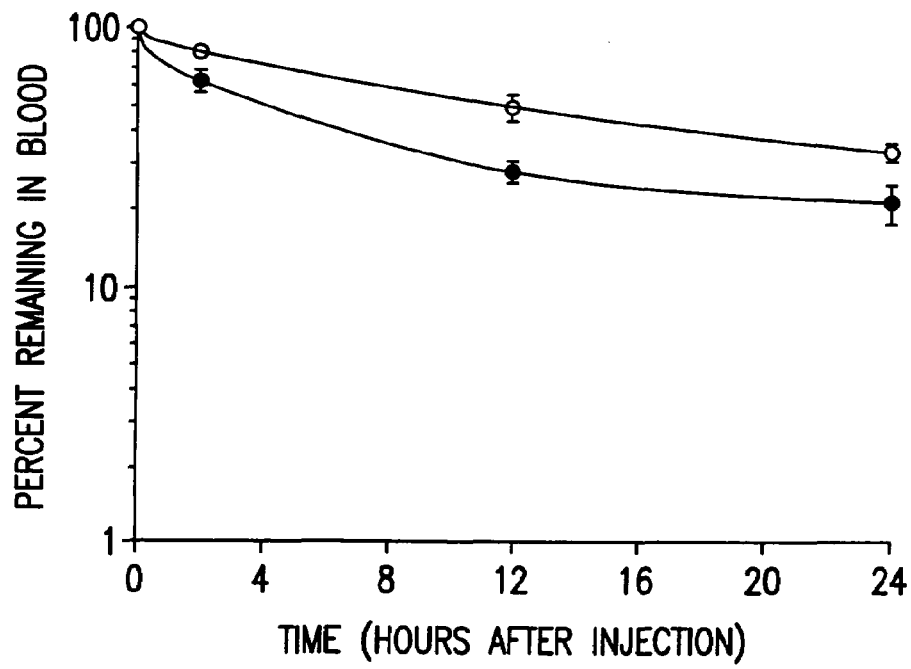
Figure 3B:
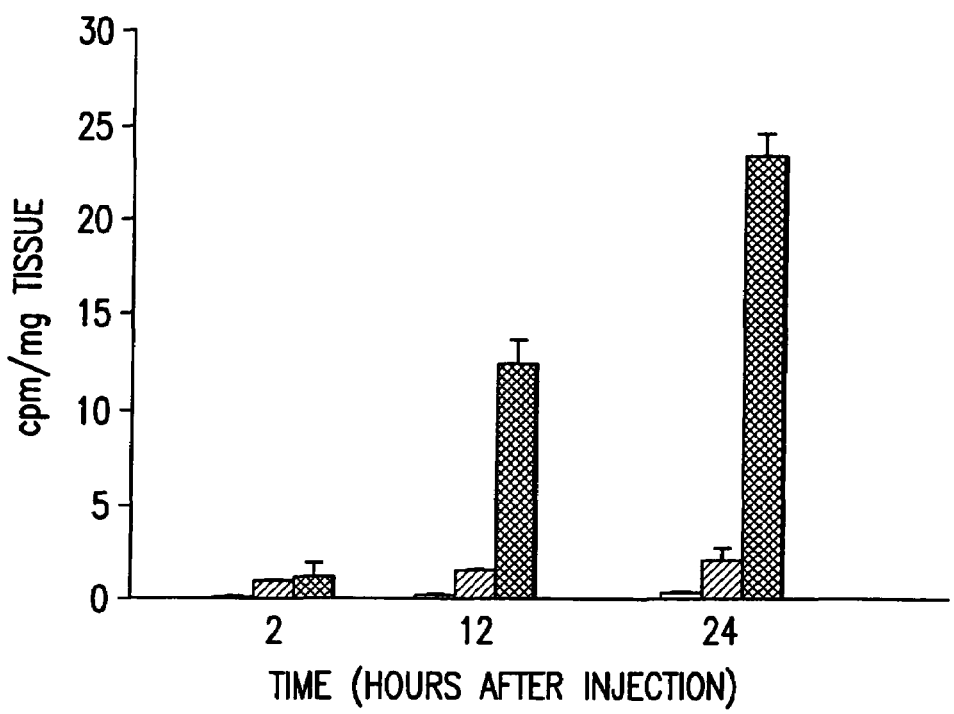
Figure 3E:
Figure 3H:
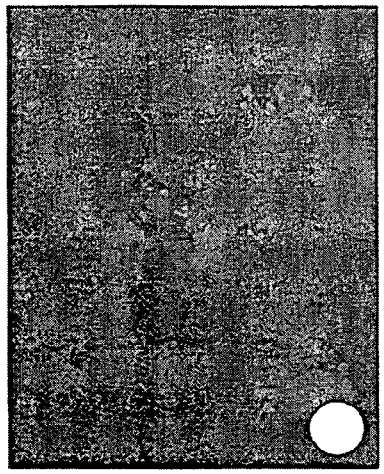

FIGS. 3a-3h. FIG. 3a shows the blood clearance kinetics of non-targeted and NGR-targeted liposomes in SCID mice. Liposomes were labeled with the lipid tracer [$^3$H]-CHE and were administered i.v. in a single bolus dose (0.5 μmol PL/mouse). Treatment groups consisted of NGR-SL (•) and SL (o). At different times post-injection, blood was collected and counted for $^3$H label. Each point represents the average of three mice±S.D. FIG. 3b shows tumor accumulation of NGR-targeted liposomes in SCID mice injected orthotopically with NB cells [$^3$H]-labeled liposomes, either non-targeted (hatched bar), ARA-targeted (white bar) or NGR-targeted (crosshatched bar) were injected via the tail vein as a single bolus dose. After 2, 12, and 24 h, tumors were collected and counted for $^3$H label. Results are expressed as cpm per mg tissue. Each point represents the average of three mice (±S.D.). Tumor accumulation of NGR-targeted liposomal DXR Mice were treated with NGR-SL[DXR] as in FIG. 3b. After 2 (FIG. 3c), 12 (FIG. 3d), and 24 (FIG. 3e) hours, tumors were collected and DXR visualized by fluorescence microscopy of fixed, paraffin embedded, tissue sections. Alternatively, mice were injected with control ARA-SL [DXR] (FIG. 3f), with NGR-SL[DXR] either alone (FIG. 3g) or co-injected with a 50-fold excess of the soluble NGR peptide (FIG. 3h). Magnitude ×40.

Figure 4A:
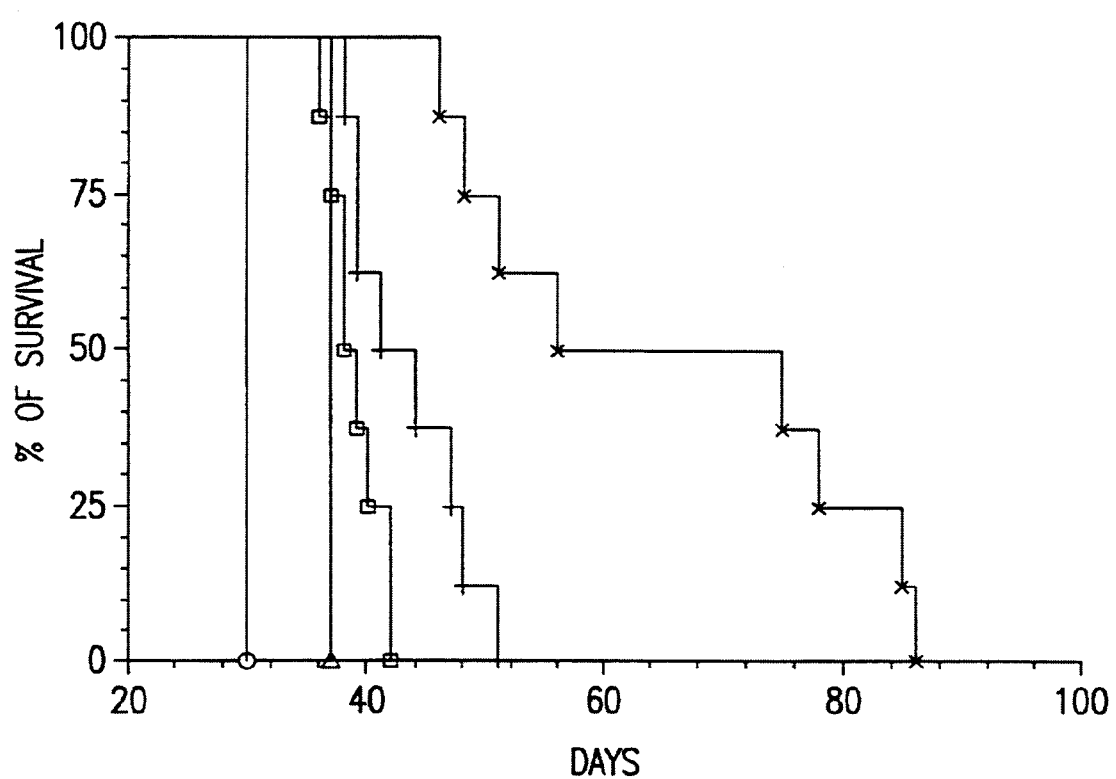

FIGS. 4a-4m. Anti-tumor effects of NGR-targeted liposomal DXR in vivo. FIG. 4a shows the dose-dependent effects of NGR-SL[DXR] on the survival of tumor-bearing mice. The treatment groups (n=8/group) consisted of HEPES buffer (control, open square), NGR-SL[DXR] at 8 mg/kg (o), 4 mg/kg (Δ), 2 mg/kg (×), and 1 mg/kg (+). Mice received injections in the adrenal gland with SH-SY5X cells on day 0 and received the various treatments 21, 28, and 35 days post-inoculation. Mice were inoculated and treated as in panel a, then photographed on day 36: FIG. 4b, control; FIG. 4c, treated with 1 mg/kg/week; FIG. 4d, treated with 2 mg/kg/week FIGS. 4e-4m, IHC analysis. Tumors were harvested on day 36 from control mice (FIGS. 4e, 4h, 4k) and mice treated with 1 mg/kg/week (FIGS. 4f, 4i, 4l) or 2 mg/kg/week (FIGS. 4g, 4l, 4m) as in panel a. Tissue sections were immunostained for the expression of factor VIII (to show vessels, FIGS. 4e, 4f, 4g; magnitude ×10) or for a double label of Factor VIII (endothelial cells) and TUNEL (apoptosis) (FIGS. 4h, 4i, 4j) or for a double label of NB84a (NB cells) and TUNEL (FIGS. 4k, 4l, 4m). Red, Factor VIII+ endothelial cells or NB84a+ neuroblastoma cells; green, TUNEL$^+$ cells; yellow, co-localization of TUNEL$^+$-factor VIII$^+$ or -NB84a$^+$ cells. FIGS. 4h-4m, ×40 magnification.

Figure 5A:
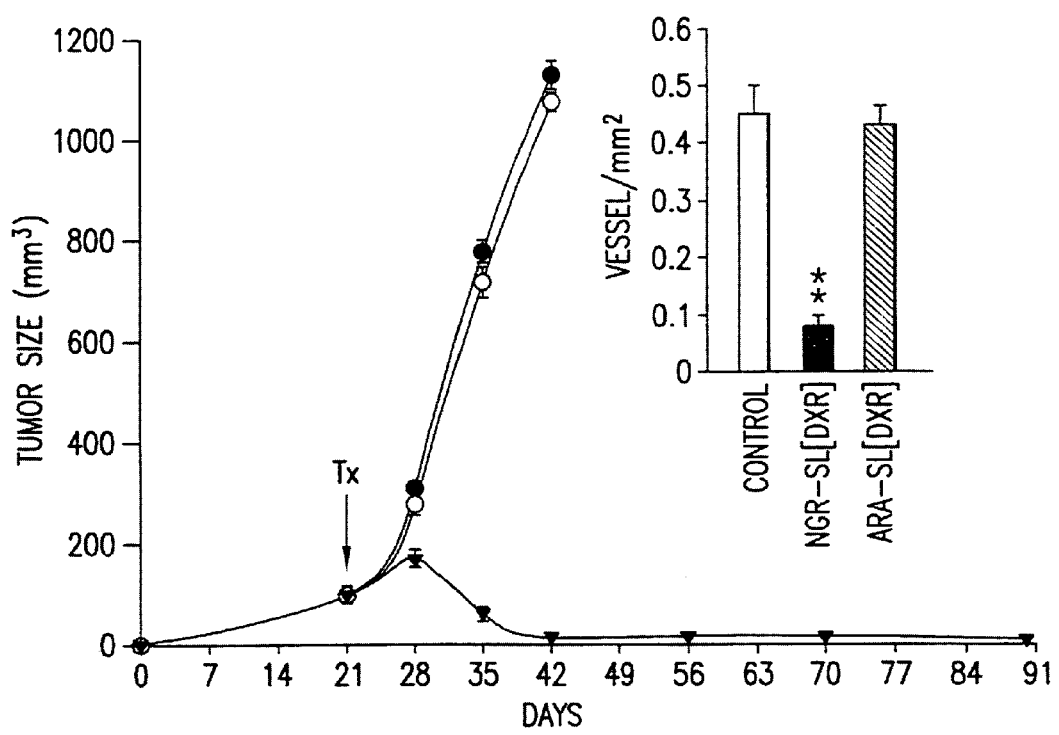

FIGS. 5a-5d. Delivery of DXR to tumor vessels inhibits angiogenesis, causing regression of established NB tumors. FIG. 5a shows SCID mice ortbotopieally implanted in the left adrenal gland with NB cells were allowed to form tumors of ~200 mm$^3$ in size and were then injected intravenous with 3 mg DXR/kg/week as in FIG. 4. Tx, start of treatment. (close circle) HEPES buffer control; (o) ARA-SL[DXR]; (black triangle) NGRSL[DXR]. Each point represents the mean±S.D. of six replicates. (Inset) Orthotopic tumors, at day 36 from control and DXR-treated groups, were sectioned and stained with an antibody to factor VIII to count blood vessels. Each bar represents the mean±S.D. of five replicates. Mice were treated as above and on day 36 organs (liver, FIG. 1b; kidney, FIG. 1c) were harvested and weighed. Each bar represents the mean±S.D. of six mice. (Asterisks, P<0.01). Effects of different schedules of treatment with NGR-SL [DXR] on lifespan. Treatment groups (n=8/group) consisted of HEPES buffer (control, □); free DXR (Δ) or NGR-SL [DXR] (+), treated with 3 mg/kg on day 21, 28, and 35; free DXR (o) or NGR-SL[DXR] (×) treated with 1 mg/kg every other two days starting on day 21, for a total of nine injections.

5. DETAILED DESCRIPTION OF THE INVENTION

The invention relates to a novel approach for cancer treatment and prevention. Specifically, the invention relates to a tumor-targeted drug delivery system that delivers a therapeutic agent to tumor cells or tumor-supporting cells. The targeted drug delivery system selectively inhibits or destroys the endothelial cells of the tumor vasculature (using angiolytic, anti-angiogenic or anti-vascular drugs, respectively) and therefore, triggers tumor growth inhibition, regression and/or a state of dormancy. A strategy that targets both the tumor-supporting cells (e.g., tumor vasculature cells) and the tumor cells themselves may be more effective than strategies that target only the tumor vasculature cells, since this latter strategy can leave a cuff of unaffected tumor cells at the tumor periphery that can subsequently re-grow and kill the animals (Huang, et al. Science 275, 547-50 (1997)).

As such, the inventors have designed a drug delivery system that delivers an increased amount of therapeutics to tumor cells and tumor-supporting cells as compared to other delivery systems. The delivery systems of the invention are stable in vivo to effectively deliver a therapeutic to the actively targeted endothelial cells and the passively targeted tumor cells, generally applicable to a wide range of cancers and diseases, and have low cytotoxicity in normal (or non-targeted) tissue while retaining their effectiveness against neoplastic (or targeted) tissue. The delivery systems of the present invention also have enhanced efficacy and enhanced efficacy compared to other ligand-targeting liposomes, specifically, as compared to other parenteral delivery systems.

One of the most unexpected findings of the present inventors is that following intravenous administration, NGR-liposomes accumulate at the tumor site in a much greater extent than corresponding liposomes that are either lacking the ligand, bearing a different ligand (such as RGD), or bearing an irrelevant ligand. The present invention demonstrates a 10-folds increase in liposome accumulation in neuroblastoma tumor twenty-four hours after administration of the NGR-liposomes as compared to a non-targeted liposome.

On the contrary, liposomes having the RGD motif instead of the NGR motif (both recognizing tumor endothelial cell markers) do not significantly accumulate more in solid colon carcinoma tumors than corresponding liposomes either lacking the ligand or bearing an irrelevant peptide (RAD containing control peptide) at 24 h post-injection.

Accordingly, in certain embodiments, the delivery system comprises a NGR-containing molecules linked to an encapsulating delivery vehicle, such as a liposome, that comprises a therapeutic agent, and is capable of delivering at least 0.5-2 folds, 2-5 folds, 5-10 folds, 15-20 folds, 20-30 folds, or 30-40 folds increase of the drug to a disease cell or a disease-supporting cell over a period of time as compared to other non-targeted drug delivery systems as well as targeted drug delivery systems. The amount of drug delivered to the disease cell(s) or disease-supporting cell(s) is sufficient to result in concentrations of the therapeutic agent above the minimal effective concentration required for a therapeutic effect In specific embodiments, a tumor cell or tumor-supporting cells is exposed to 2-10%, 10-20%, 20-30%, 30-40%, 40-50%, 50-60%, 60-70%, 70-80%, 80-90%, or 90-99% of therapeutic agent over a period of at least 2-5 hours, 5-10 hours, 10-12 hours, 12-24 hours, 24-36 hours, 36-48 hours, 3-5 days, 5-7 days, or 1-3 weeks as compared to other drug delivery system.

In specific embodiments, the amount of therapeutic agent that may be accumulated in a tumor using the systems and methods of the present invention is at least 5-7 mg/g, 7-10 mg/g, 10-50 mg/g, 50-70 mg/g, 70-100 mg/g, 100-150 mg/g, or 150-200 mg/g of tumor. In specific embodiments, the therapeutic agent accumulated in the tumor is doxorubicin ("DXR").

The targeted drug delivery system of the invention increases the therapeutic effect for drugs in targeted cells and decreases the toxicity for drugs against non-targeted cells, thereby increasing the therapeutic index for the drug, wherein therapeutic index is defined as efficacy over toxicity.

In one embodiment, the NGR-containing molecule binds to a tumor-supporting cells, preferably a tumor vascular endothelial cell. In a specific embodiment, the NGR-containing molecule binds to a cell that expresses an NGR receptor. In preferred embodiments, the NGR-containing molecule is a circular or linear peptide, polypeptide, protein, or derivatives thereof, comprising NGRAHA (SEQ ID NO:1), GNGRG (SEQ ID NO:2), CNGRC (SEQ ID NO:3), CNGRCVSGCAGRC (SEQ ID NO:4), CVLNGRMEC (SEQ ID NO:5), GNGRGGVRSSSRTPSDKYC (SEQ ID NO:6), or one or more of the amino acid sequences of SEQ ID NOS:1-6.

In one embodiment, the encapsulating delivery vehicle can be a liposome, micelle, lipidic micelle, microsphere, nanosphere, chambered microdevice, emulsion, lipid disc, polymer, cell, viral particle or virus. Preferably, the delivery vehicle is a liposome. The liposome comprise lipids or lipopolymers, such as, but not limited to, one or more methoxypolyethylene glycol phosphatidylethanolamine, maleimidopolyethylene glycol phosphatidylethanolamine, N-methylpalmitoyloleoylphosphatidylcholine, phosphatidylserine, phosphatidylcholine, palmitoyloleoylphosphatidylcholine, dipalmitoylphosphatidylcholine, distearoylphosphatidylcholine, diphytanoylphosphatidylcholine, sphinomyelin, phosphatidylglycerol, cholesterol ("CHOL"), or a combination thereof. To those skilled in the art, liposomes may be composed of other bilayer-forming lipids or lipo-polymers and cholesterol. Preferably, the delivery vehicle is composed of a bilayer-forming lipid, such as phospholipid and cholesterols, and contains a polyethyleneglycol ("PEG")-derivatized lipid within the bilayer. More preferably, the delivery vehicle is a bilayer vesicle with a PEG-derivatized distearoylphosphatidylethanolamine ("PEG-DSPE") grafted to the bilayer (i.e., a "sterically stabilized" liposome).

In one embodiment, the drug is a cytotoxic drug, an anticancer drug, an anti-inflammatory drug, and an anti-angiogenic or angiolytic drug. In another embodiment, the drug is encapsulated, entrapped, intercalated, within the core, or associated with the delivery vehicle.

In a specific embodiment, the plurality of NGR-containing molecule are operably linked to the encapsulating delivery vehicle through a linking agent.

Methods of making the delivery systems are described below in Section 5.1. Methods of using the delivery system of the invention are described below in Section 5.2.

5.1 Construction of a Tumor Targeted Drug Delivery System

The tumor cell-targeted drug delivery system of the present invention comprises one or more NGR-containing molecules (Section 5.1.1 ) linked to an encapsulating delivery vehicle (Section 5.1.2) comprising a prophylactic or therapeutic agent (Section 5.1.3)

5.1.1 NGR-Containing Molecules

In certain embodiments, the NGR-containing molecule binds to a receptor that is expressed in tumor vessels but not expressed in normal endothelial cells. In a preferred embodiment, the NGR-containing peptide binds to aminopeptidase N (CD13), a trans-membrane glycoprotein of 150 kDa that is highly conserved in various species. CD13 is expressed on normal cells as well as in myeloid tumor lines, in angiogenic endothelial tissue and in some epithelial tissues. A CD13 receptor is usually identified as an "NGR" receptor.

As a ligand of the CD13 receptor, the NGR-containing molecule can be also be an CD13-binding antibody or a fragment thereof such as Fab, Fv, single-chain Fv, a peptide or a peptido-mimetic, namely a peptido-like molecule capable to bind the CD13 receptor, optionally containing modified, not naturally occurring amino acids that contain an NGR-peptide.

The NGR-containing molecule may be natural or synthetic. In preferred embodiments, the molecule is a peptide, polypeptide, protein or derivatives thereof. The molecule may also be a modified peptide, polypeptide, protein, or derivatives thereof. In certain embodiments, the molecule is chemically modified. The one or more binding domains of the NGR-containing molecule may consist of, for example, a natural ligand for the CD13 receptor, or a fragment of a natural ligand which retains binding affinity for the CD13 receptor. Synthetic ligands include the designer ligands. As used herein, "designer ligands" refer to agents which are likely to bind to the receptor based on their three dimensional shape compared to that of the receptor.

A number of ligands to the CD13 receptor are described in International Publication No. WO98/10795, which is incorporated herein by reference in its entirety. Methods of identifying ligands of CD13 receptor are disclosed in International Publication No. WO99/13329, which is incorporated herein by reference in its entirety.

As a ligand to the CD13 receptor, the NGR-containing molecule is preferably a straight (linear) or cyclic peptide comprising an NGR motif. In one embodiment, the NGR-containing molecule comprises NGRAHA (SEQ ID NO:1), GNGRG (SEQ ID NO:2), CNGRC (SEQ ID NO:3), CNGRCVSGCAGRC (SEQ ID NO:4), CVLNGRMEC (SEQ ID NO:5), or GNGRGGVRSSSRTPSDKYC (SEQ ID NO:6). In another embodiment, the NGR-containing molecule comprises one or more of the amino acid sequences of SEQ ID NOS:1-6.

In certain other embodiments, the NGR-containing molecule comprises a GNGRG motif. In a specific embodiment, the NGR-containing molecule comprises a GNGRG motif and a TNF N-terminal sequence. Preferably the TNF N terminal sequence comprises the amino acid sequence VRSSSRTPSD (SEQ ID NO:7). In another specific embodiment, the NGR-containing molecule comprises a GNGRG motif followed by a TNF N-terminal sequence and ending with a N-terminal cysteine. In one embodiment, the NGR-containing molecule is GNGRGGVRSSSRTPSDKYC (SEQ ID NO:6)

In another embodiment, the NGR-containing molecule binds an $\alpha_v$ integrin or a receptor for angiogenic growth factor.

In another embodiment, the NGR-containing molecule binds to a TNF receptor. In a specific embodiment, the NGR-containing molecule binds to members of the TNF receptor superfamily (TNFSF). Molecules in the TNFRSF are all type I (N-terminus extracellular) transmembrane glycoproteins that contain one to six ligand-binding, 40 amino acid residue cysteine-rich motifs in their extracellular domain. In addition, functional TNFRSF members are usually trimeric or multi-meric complexes that are stabilized by intracysteine disulfide bonds. Unlike most members of the TNFSF, TNFRSF members exist in both membrane-bound and soluble forms. Finally, although amino acid sequence homology in the cytoplasmic domains of the superfamily members does not exceed 25%, a number of receptors are able to transduce apoptotic signals in a variety of cells, suggesting a common function.

In another specific embodiment, the NGR-containing molecule binds to CD40, a 50 kDa, 277 amino acid residue transmembrane glycoprotein most often associated with B cell proliferation and differentiation. Expressed on a variety of cell types, human CD40 cDNA encodes a 20 amino acid residue signal sequence, a 173 amino acid residue extracellular region, a 22 amino acid residue transmembrane segment, and a 62 amino acid residue cytoplasmic domain. There are four cysteine-rich motifs in the extracellular region that are accompanied by a juxtamembrane sequence rich in serines and threonines. Cells known to express CD40 include endothelial cells.

In another specific embodiment, the NGR-containing molecule binds to TNFRI/p55/CD120a. TNFRI is a 55 kDa, 455 amino acid residue transmembrane glycoprotein that is apparently expressed by virtually all nucleated mammalian cells. The molecule has a 190 amino acid residue extracellular region, a 25 amino acid residue transmembrane segment, and a 220 amino acid residue cytoplasmic domain. Both TNF-α and TNF-β bind to TNFRL. Among the numerous cells known to express gNFRI are endothelial cells.

In another specific embodiment, the NGR-containing molecule binds to TNFII/p75/CD120b. Human TNFRII is a 75 kDa, 461 amino acid residue transmembrane glycoprotein originally isolated from a human lung fibroblast library. This receptor consists of a 240 amino add residue extracellular region, a 27 as residue transmembrane segment and a 173 amino acid residue cytoplasmic domain. Soluble forms of TNFRII have been identified, resulting apparently from proteolytic cleavage by a metalloproteinase termed TRRE (TNF-Receptor Releasing Enzyme). The shedding process appears to be independent of that for soluble TNFRI. Among the multitude of cells known to express TNFRII are endothelial cells.

In another specific embodiment, the NGR-containing molecule binds to CD134/OX40L. OX40, the receptor for OX40L, is a T cell activation marker with limited expression that seems to promote the survival (and perhaps prolong the immune response) of CD4+ T cells at sites of inflammation. OX40L also shows limited expression. Currently only activated CD4+, CA8+ T cells, B cells, and vascular endothelial cells have been reported to express this factor. The human ligand is a 32 kDa, 183 amino acid residue glycosylated polypeptide that consists of a 21 amino acid residue cytoplasmic domain, a 23 amino acid residue transmembrane segment, and a 139 amino acid residue extracellular region.

In another specific embodiment, the NGR-containing molecule binds to a VEGF receptor. There are three receptors in the VEGF receptor family. They have the common properties of multiple IgG-like extracellular domains and tyrosine kinase activity. The enzyme domains of VEGF receptor 1 (VEGF R1, also known as Flt-1); VEGF R2 (also known as KDR or Flk-1), and VEGF R3 (also known as Flt-4) are divided by an inserted sequence. Endothelial cells also express additional VEGF receptors, Neuropilia-1 and Neuropilin-2. VEGF-A binds to VEGF R1 and VEGF R2 and to Neuropilitu-1 and Neuropilin-2. PIGF and VBGF-B bind VEGF R1 and Neuropilin-1. VEGF-C and -D bind VEGF R3 and VEGF R2. HIV-tat and peptides derived therefrom have also been found to target the VEGFR.

In another specific embodiment, the NGR-containing molecule binds to a PDGF receptor. PDGF receptors are expressed in the stromal compartment in most common solid tumors. Inhibition of stromally expressed PDGF receptors in a rat colon carcinoma model reduces the tumor interstitial fluid pressure and increases tumor transcapillary transport.

In another specific embodiment, the NGR-containing molecule binds to a prostate specific membrane antigen (PSMA), which are expressed in the stromal compartment in most common solid tumors. Inhibition of stromally expressed PDGF receptors in a rat colon carcinoma model reduces the tumor interstitial fluid pressure and increases tumor transcapillary transport.

In another specific embodiment, the NGR-containing molecule binds to cell adhesion molecules (CAMs), which cell surface proteins involved in the binding of cells, usually leukocytes, to each other, to endothelial cells, or to extracellular matrix. Specific signals produced in response to wounding and infection control the expression and activation of certain of these adhesion molecules. The interactions and responses then initiated by binding of these CAMS to their receptors/ligands play important roles in the mediation of the inflammatory and immune reactions that constitute one line of the body's defense against these insults. Most of the CAMS characterised so far fall into three general families of proteins: the immunoglobulin (Ig) superfamily, the integrin family, or the selectin family.

In other specific embodiments, the NGR-containing molecule binds to the following molecules as listed below:

A member of the Selectin family of cell surface molecules, L-Selectin consists of an NH2-terminal lectin type C domain, an EGF-like domain, two complement control domains, a 15 amino acid residue spacer, a transmembrane sequence and a short cytoplasmic domain.

Three ligands for L-Selectin on endothelial cells have been identified, all containing 0-glycosylated mucin or mucin-like domains. The first ligand, GlyCAM-1, is expressed almost exclusively in peripheral and mesenteric lymph node high endothelial venules. The second L-Selectin ligand, originally called sgp90, has now been shown to be CD34. This sialomucin-like glycoprotein, often used as a surface marker for the purification of pluripotent stem cells, shows vascular expression in a wide variety of nonlymphoid tissues, as well as on the capillaries of peripheral lymph nodes. The third ligand for L-Selectin is MadCAM 1, a mucin-like glycoprotein found on mucosal lymph node high endothelial venules.

P-Selectin, a member of the Selectin family of cell surface molecules, consists of an NH2-terminal lectin type C domain, an EGF-like domain, nine complement control domains, a transmembrane domain, and a short cytoplasmic domain.

The tetrasaccharide sialyl Lewisx (sLex) has been identified as a ligand for both P- and E-Selectin, but P- E- and L-Selectin can all bind sLex and sLea under appropriate conditions. P-Selectin also reportedly binds selectively to a 160 kDa glycoprotein present on murine myeloid cells and to a glycoprotein on myeloid cells, blood neutrophils, monocytes, and lymphocytes termed P-Selectin glycoprotein ligand-1 (PSGL-1), a ligand that also can bind E-Selectin. P-Selectin-mediated rolling of leukocytes can be completely inhibited by a monoclonal antibody specific for PSLG-1, suggesting that even though P-Selectin can bind to a variety of glycoproteins under in vitro conditions, it is likely that physiologically important binding is more limited. A variety of evidence indicates that P-Selectin is involved in the adhesion of myeloid cells, as well as B and a subset of T cells, to activated endothelium.

The Ig superfamily CAMS are calcium-independent transmembrane glycoproteins. Members of the Ig superfamily include the intercellular adhesion molecules (ICAMs), vascular-cell adhesion molecule (VCAM-1), platelet-endothelial-cell adhesion molecule (PECAM-1), and neural-cell adhesion molecule (NCAM). Each Ig superfamily CAM has an extracellular domain, which contains several Ig-like intrachain disulfide-bonded loops with conserved cysteine residues, a transmembrane domain, and an intracellular domain that interacts with the cytoskeleton. Typically, they bind integrins or other Ig superfamily CAMs. The neuronal CAMs have been implicated in neuronal patterning. Endothelial CAMs play an important role in immune response and inflammation.

In more detail, vascular cell adhesion molecule (VCAM-1, CD106, or INCAM-110), platelet endothelial cell adhesion molecule (PECAM-I/CD31) and intercellular adhesion molecules 1, 2 & 3 (ICAM-1, 2 & 3) are five functionally related CAM/IgSF molecules that are critically involved in leukocyte-connective tissue/endothelial cell interactions. Expressed principally on endothelial cells, these molecules in general regulate leukocyte migration across blood vessel walls and provide attachment points for developing endothelium during angiogenesis and are all suitable for targeting in the present invention.

Human CD31 is a 130 kDa, type I (extracellular N-terminus) transmembrane glycoprotein that belongs to the cell adhesion molecule (CAM) or C2-like subgroup of the IgSFl. The mature molecule is 711 amino acid residues in length and contains a 574 amino acid residue extracellular region, a 19 amino acid residue transmembrane segment, and a 118 amino acid glycoprotein that contains a number of peptide motifs. Cells reported to express FGF-3 are limited to developmental cells and tumors. Tumors known to express FGF-3 include breast carcinomas and colon cancer cell lines.

Human FGF-4 is a 22 kDa, 176 amino acid glycoprotein that is the product of a developmentally-regulated gene. The molecule is synthesized as a 206 amino acid precursor that contains a large, ill-defined 30 amino acid signal sequence plus two heparin-binding motifs (at amino acids amino acids 51-55 and 140-143). The heparin binding sites directly relate to FGF-4 activity; heparin/heparan regulate the ability of FGF-4 to activate FGFRI and FGFR2. Cells known to express FGF-4 include both tumor cells and embryonic cells. Its identification in human stomach cancer-gives rise to one alternative designation (/hst-1/hst), while its isolation in Kaposi's sarcoma provides grounds for another (K-FGF).

In another specific embodiment, the NGR-containing molecule binds to IL-1R. Two distinct IL-1 receptor binding proteins, plus a non binding signaling accessory protein have been identified. Each have three extracellular immunoglobulin-like (Ig-like) domains, qualifying them for membership in the type N cytokine receptor family. The two receptor binding proteins are termed type I IL-I receptor (IL1 RI) and type II 1L-1 receptor (IL-1 RII) respectively. Human IL-1 RI is a 552 amino acid residue 80 kDa transmembrane glycoprotein that has been isolated from endothelium cells.

In another specific embodiment, the NGR-containing molecule binds to a receptor tyrosine kinase (RTK). The new family of receptor tyrosine kinase (RTK), the Eph receptors and their ligands ephrins, have been found to be involved in vascular assembly, angiogenesis, tumorigenesis, and metastasis. It has also been that class A Eph receptors and their ligands are elevated in tumor and associated vasculature.

In another specific embodiment, the NGR-containing molecule binds to matrix metalloproteinases (MMPs), which have been implicated in tumor growth, angiogeneeas, invasion, and metastasis. They have also been suggested for use as tumor markers.

In another specific embodiment, the NGR-containing molecule binds to NG2, which is a large, integral membrane, chondroitin sulfate proteoglycan that was first identified as a cell surface molecule expressed by immature neural OF-11S. Subsequently NG2 was found to be expressed by a wide variety of immature cells as well as several types of tumors with high malignancy. NG2 has been suggested as a target molecule in the tumor vasculature. In particular, eollagenase-1 (Cl) is the predominant matrix metalloproteinase present in newly formed microvessels and serves as a marker of neovascularization.

In another specific embodiment, the NGR-containing molecule binds to oncofetal fibronectin. The expression of the oncofetal fragment of fibronectin (Fn-f) has also been found to be increased during angiogenesis and has been suggested as a marker of tumor angiogenesis. In one embodiment, the NGR-containing molecule is an antibody or fragment thereof to the oncofetal ED-B domain of fibronectin. The preparation of such an antibody and its conjugation with IL-12 is described in Halin et al (2002) Nature Biotechnology 20:264-269, which is incorporated by reference herein in its entirety.

In another specific embodiment, the NGR-containing molecule binds to tenascin. Tenascin is a matrix glycoprotein seen in malignant tumors including brain and breast cancers and melanoma. Its expression is malignant but not well differentiated tumors and association with the blood vessels of tumors makes it an important target for both understanding the biology of malignant tumors and angiogenesis, but is a therapeutic cancer target and marker as well.

It will be appreciated that one can apply conventional protein binding assays to identify molecules which bind to surface molecules. It will also be appreciated that one can apply structural based drug design to develop sequences which bind to surface molecules. High throughput screening, as described above for synthetic compounds, can also be used for identifying targeting molecules. This invention also contemplates the use of competitive drug screening assays in which neutralizing antibodies capable of binding a target specifically compete with a test compound for binding to a target.

In certain embodiments, the NGR-containing molecule binds to any one or more of the above-mentioned receptors, or fragments, analogs, derivatives or variants thereof.

In certain embodiments, the NGR-containing molecules are covalently attached to the delivery vehicle via a linker group. In one embodiment, the NGR-containing molecules are attached to the delivery vehicle via a hydrophilic polymer. There are a wide variety of techniques for attaching a hydrophilic polymer to a targeting domain, and in particular the hydrophilic polymer polyethyleneglycol (PEG) is widely used. The PEG chains may be functionalized to contain reactive groups suitable for coupling with, e.g., sulfhydryls, amino groups, and aldehydes and ketones present in many targeting domains. Examples of such PEG terminal reactive groups include maleimide, hydrazide, M-hydroxysuccinimide (NHS) or NHS-carbonate ester, hydrazide or hydrazine, iodoacetyl and dithiopyridine.

As described in the example in Section 6, in one embodiment, in order to enhance the accessibility of the NGR-containing molecules when bound to the delivery vehicle, and to permit coupling via a thiol to a maleimido moiety on the delivery vehicle, additional residues can be added to the peptide amino terminus to provide the peptide GNGRG-GVRSSSRTPSIDKYC (SEQ ID NO:6).

5.1.2 Liposomes

Liposomes are small vesicles composed of lipids arranged in spherical bilayers. Liposomes are usually classified as small unilamellar vesicles (SUV), large unilamellar vesicles (LUV), or multi-lamellar vesicles (MLV). SUVs and LUVs, by definition, have only one bilayer, whereas MLVs contain many concentric bilayers (see, e.g., Stryer, *Biochemistry, 2d Edition,* W.H. Freeman & Co., p. 213 (1981)).

Liposomes may be prepared by a variety of techniques (see, e.g., Szoka, F., Jr., et al., *Ann. Rev. Biophys. Bioeng.* 9:467 (1980); U.S. Pat. No. 5,631,018). Liposomes are generally prepared from phospholipids and generally contain cholesterol. In one embodiment, the liposomes comprise non-polymerized or minimally polymerized phospholipids. In another embodiment, the liposomes are prepared by polymerization of double and triple bond-containing monomeric phospholipids. In a preferred embodiment, examples of polymerizable functional groups, include but are not limited to olefins, acetylenes, acrylates and thiols. The liposomes of the present invention may be polymerized by a variety of techniques known to those skilled in the art including but not limited to free radical initiation and ultraviolet and gamma irradiation. Suitable phospholipids are known to those skilled in the art, and include, but are not limited to, phosphatidylcholines, sphingomyelins, phosphatidylglycerols, phosphatidylinositols, phosphatidylserines, phosphatidic acids, DODPC (1,2-di(2,4-Octadecadienoyl)-3-phosphatidylcholine), 2,4-diene phospholipids, di-yne phospholipids, see e.g., U.S. Pat. Nos. 4,485,045 and 4,861,521, which are incorporated herein by reference in their entireties.

Liposomes suitable for use in the composition of the present invention include those composed primarily of vesicle-forming lipids. Vesicle-forming lipids can form spontaneously into bilayer vesicles in water, as exemplified by the phospholipids. The liposomes can also include other lipids incorporated into the lipid bilayers, e.g., cholesterol, with the hydrophobic moiety in contact with the interior, hydrophobic region of the bilayer membrane, and the head group moiety oriented toward the exterior, polar surface of the bilayer membrane.

The vesicle-forming lipids are preferably ones having two hydrocarbon chains, typically acyl chains, and a head group, either polar or nonpolar. There are a variety of synthetic vesicle-forming lipids and naturally-occurring vesicle-forming lipids, including the phospholipids, such as phosphalidylcholine, phosphatidylethanolaamine, phosphatidic acid, phosphatidylinositol, and sphingomyelin, where the two hydrocarbon chains are typically between about 14-22 carbon atoms in length, and have varying degrees of unsaturation. The above-described lipids and phospholipids whose acyl chains have varying degrees of saturation can be obtained commercially or prepared according to published methods. Other suitable lipids include glycolipids and sterols, such as cholesterol.

In one embodiment, the vesicle-forming lipid is selected to achieve a specified degree of fluidity or rigidity, to control the stability of the liposome in serum and to control the rate of release of the entrapped agent in the liposome.

Liposomes having a more rigid lipid bilayer, or a liquid crystalline bilayer, are achieved by incorporation of a relatively rigid lipid, e.g., a lipid having a relatively high phase transition temperature, e.g., above room temperature, more preferably above body temperature and up to 80° C. Rigid, i.e., saturated, lipids contribute to greater membrane rigidity in the lipid bilayer. Other lipid components, such as cholesterol, arc also known to contribute to membrane rigidity in lipid bilayer structures.

On the other hand, lipid fluidity is achieved by incorporation of a relatively fluid lipid, typically one having a lipid phase with a relatively low liquid to liquid-crystalline phase transition temperature, e.g., at or below room temperature, more preferably, at or below body temperature.

Vesicle-forming lipids having a main phase transition temperatures from approximately 2-80° C. are suitable for use as the primary liposome component of the present composition. In a preferred embodiment of the invention, a vesicle-forming lipid having a main phase transition temperature above about 37° C. is used as the primary lipid component of the liposomes. In another preferred embodiment, a lipid having a phase transition temperature between about 37-70° C. is used. By way of example, the lipid distearoyl phosphatidylcholine (DSPC) has a main phase transition temperature of 55.1° C. and the lipid. hydrogenated soy phosphatidylcholine (HSPC) has a phase transition temperature of 58° C. Phase transition temperatures of many lipids are tabulated in a variety of sources, such as Avanti Polar Lipids catalogue and Lipid Thermotropic Phase Transition Database (LIPIDAT, NLST Standard Reference Database 34).

The liposomes also include a vesicle-forming lipid derivatized with a hydrophilic polymer. As has been described, for example in U.S. Pat. No. 5,013,556 and in International Publication No. WO 98/07409, which are hereby incorporated by reference in their entireties, such a hydrophilic polymer provides a surface coating of hydrophilic polymer chains on both the inner and outer surfaces of the liposome lipid bilayer membranes. The outermost surface coating of hydrophilic polymer chains is effective to provide a liposome with a long blood circulation lifetime in vivo. The inner coating of hydrophilic polymer chains extends into the aqueous components in the liposomes, i.e., between the lipid bilayers and into the central core compartment, and is in contact with the entrapped compound after the compound is loaded via remote loading.

Vesicle-forming lipids suitable for derivatization with a hydrophilic polymer include any of those lipids listed above, and, in particular phospholipids, such as distearoyl phosphatidylethanolamine ("DSPE"). In a preferred embodiment the liposome may comprise fully hydrogenated soy phosphatidylcholine ("HSPC") or distearoylphosphatidylcholine ("DSPC") and/or cholesterol ("CHOL"). In a particularly preferred embodiment, the liposome is composed of N-(carbonyl-methoxypolyethylene glycol 2000)-1,2-distearoyl-sn glycero-3-phosphatidylethanolamine sodium salt ("mPEG-DSPE").

Hydrophilic polymers suitable for derivatization with a vesicle-forming lipid include polyvinylpyrrolidone, polyvinylmethylether, polymethyloxazoline, polyethyloxazoline, polyhydroxypropyloxaz line, polyhydroxypropylmethacrylamide, polymehacrylamide, polyduuctbylacrylamid polyhydroxypropylmethacrylate, polyhydroxyethylacrylate, hydroxymethylcellulose, hydroxyethylcellulose, polyethyleneglycol, and polyaspartamide. The polymers may be employed as homopolymers or as block or random copolymers.

A preferred hydrophilic polymer chain is polyethyleneglycol (PEG), preferably as a PEG chain having a molecular weight between 500-10,000 daltons, more preferably between 500-5,000 daltons, most preferably between 1,000-2,000 daltons. Methoxy- or ethoxy-capped analogues of PEG are also preferred hydrophilic polymers, commercially available in a variety of polymer sizes, e.g., 120-20,000 daltons.

Preparation of vesicle-forming lipids derivatized with hydrophilic polymers has been described, for example, in U.S. Pat. No. 5,395,619. Preparation of liposomes including such derivatized lipids has also been described, where, typically, between 1-20 mole percent of such a derivatized lipid is included in the liposome formulation. It will be appreciated that the hydrophilic polymer may be stably coupled to the lipid, or coupled through an unstable linkage, which allows the coated liposomes to shed the coating of polymer chains as they circulate in the bloodstream or in response to a stimulus.

Cationic lipids are also suitable for use in the liposomes of the invention, where the cationic lipid can be included as a minor component of the lipid composition or as a major or sole component. Such cationic lipids typically have a lipophilic moiety, such as a sterol, an acyl or diacyl chain, and where the lipid has an overall net positive charge. Preferably, the head group of the lipid carries the positive charge. Exemplary cationic lipids include 1,2-dioleyloxy-3-(trimethylamino) propane (DOTAP); N-[1-(2,3, ditetradecylM)propyl]-NN-dimethy N-hydroxycthylammonium bromide (AMRIE'); N[1-(2,3,-dioleyloxy)propyl]-N1N-dimethyl-N-hydroxy ethylammonium bromide (DORTE); N-[1-(2,3-dioleyloxy)propyl]N,N,N-trunethylanunonium chloride (DOTMA); 3 (N-(N',N'-dimethylaminoethane) carbamolyl cholesterol (DC-Chol); arid dimethyldioctadecylammonium (DDAB).

The cationic vesicle-forming lipid may also be a neutral lipid, such as dioleoxylphosphatidyl ethanolamine (DOPE) or an amphipathic lipid, such as a phospholipid, derivatized with a cationic lipid, such as polylysine or other polyamine lipids. For example, the neutral lipid (DOPE) can be derivatized with polylysine to form a cationic lipid.

In addition, liposomes can be prepared from phospholipids with negatively charged groups.

In another embodiment, hyaluronan-lipid derivatives are incorporated into the liposome. Preferably, the mole ratio of the lipid derivatives in the lipid composition of the liposome is more than about 0.02% and less than about 50%. Exemplary lipids to which the hyaluronan may be attached include phosphatidylethanolamine derivatives such as palmitoyloleoylphosphatidylethanolamine, dipalmitoylphosphatidylethanolamine, distearoylphosphatidylethanolamine, diphytanoylphosphatidylethanolaamine, N-methylphosphatidylethanolamine derivatives or phosphatidylserine derivatives. These exemplary lipids may further comprise amino-polyethylene glycols. Although these lipids are currently preferred, other lipids and liposome systems may also be used.

Other delivery vehicles useful in the invention include lipidic micelles, e.g., micelles composed of PEG-DSPE for use with hydrophobic drugs (see e.g., US 20020192275 on the benzophorphrins for photodynamic therapy, which is incorporated by reference herein in its entirety).

5.1.3 Therapeutic/Prophylactic Drug

Examples of cytotoxic drugs which may be used in the present invention include: alkylating drugs, such as cyclophosphamide, ifospfamide, ehlorambucil, melphalan, busulfan, lomustine, carmustine, chlormethhine (mustine), estramustine, treosulfan, thiotepa, mitobronitol; cytotoxic antibiotics, such as doxorubicin, epirubicin, aclarubicin, idarubicin, daunorubicin, mitoxantrone (mitozantrone), bleomycin, dactinomycin and mitomycin; antimetabolites, such as methotrexate, capecitabine; cytarabine, fludarabine, cladribine, gemcitabine, fluorouracil, raltitrexed (tomudex), mercaptopurine, tegafur and tioguaninc; vinca alkaloids, such as vinblastine, vincristine, vindesine, vinorelbine and etoposide; other neoplastic drugs, such as amsacrine, altetarmine, crisantaspase, dacarbazine and temozolomide, hydroxycarbamide (hydroxyurea), pentostatin, platinum compounds including: carboplatin, cisplatin and oxaliplatin, porfimer sodium, procarbazine, razoxane; taxanes including: docetaxel and paclitaxel; topoisomerase I inhibitors including inotecan and topotecan, trastuzumab, and tretinoin.

In a preferred embodiment, the cytotoxic drug is doxorubicin (DXR), vincristine, cisplatin or melphalan. In a particularly preferred embodiment, the drug is doxorubicin and especially doxorubicin hydrochloride. In preferred embodiments, the drug is calichemicin, Iressa and Gleevec.

Virtually, every conventional cytotoxic anti-cancer drug has been accidentally discovered to have anti-angiogenic or angiolytic effects in various in vitro and in vivo models (Bocci, G. et al. *Cancer Res* 62, 6938-43 (2002); Miller, supra). Interest in exploiting chemotherapeutics as anti-angiogenics or angiolytics has been stimulated by reports showing that frequent administration of low doses of various chemotherapeutic agents called "metronomic dosing" or "anti-angiogenic chemotherapy" can damage the tumor vasculature with limited host toxicity (Browder, T. et al. *Cancer Res* 60, 1878-86 (2000); Klement, G. et al. *J Clin Invest* 105, R15-24 (2000)). As such, the delivery system of the present invention may be used to deliver such anti-angiogenic or angiolytic compounds for use in the treatment of cancer.

The use of anti-inflammatory compound has also been proposed for use in the treatment of cancer. In one embodiment, the anti-inflammatory agent is a non-steroidal anti-inflammatory drug (NSAID). Non-limiting examples of NSAIDs include ibuprofen, aceclofenac, acemetacin, azapropazone, celecoxib, dexketoprofen, diclofenac sodium, diflunisal, ctodolac, fenbufen, fenoprofen, flubiprofen, indomethacin, acetaminocin, piroxicam , rofecoxib, suliudac, tenoxicam, tiaprofenuie acid, aspirin and benorilate.

The delivery system may be used to treat a condition associated with inflammation. The delivery system may also be used to treat conditions associated with angiogenesis.

Examples of angiogenesis inhibitors that may be used as the therapeutic agent include angiostatin (plasminogen fragment), anti-angiogenic antithrombin III (aaATIII), canstatin, cartilage-derived inhibitor (CDI), CD59 complement fragment, endostatin (collagen XVIII fragment), fibronectin fragment, gro-beta, heparinases, heparin hexasaccharide fragment, human chorionic gonadotropin (hCG), interferon alpha/beta/gamma, interferon inducible protein (IP-10), IL-12, kringle 5 (plasminogen fragment), metalloproteinase inhibitors, 2-niethoxyestradiol, PEDF, placental ribonuclease inhibitor, platelet factor-4, prolactin 16 kD fragment, proliferin-related protein, retinoids, tetrahydrocortisol-S, thrombospondin, transforming growth factor-beta, tumistatin, vasculostatin and vasostalin (calreticulin fragment).

The agents of the present invention may be administered alone but will generally be administered as a pharmaceutical composition. Other useful therapeutic agents that may be used in the methods of the present invention include, for example, those disclosed in Section 5.2.3.

5.1.4 Encapsulation of the Drug into the Liposomes

The following is a general method for the preparation of liposomes wherein a biologically active substance is present in the solution during the formation of the liposome. The phospholipid and, optionally, cholesterol and their adjuvants or coupling lipids, are dissolved, and the solution is then dried to form a thin lipid film. A solution containing substance to be entrapped is added. At this stage, it is preferable to establish an inert atmosphere. The lipid is then hydrated by gently shaking the mixture at a temperature of from about 20-50° C., usually around 25° C., for between five minutes and two hours, preferably around five minutes. Once the lipid film is hydrated, the trapped ratio of the liposome can be increased by performing one or more freeze-thaw cycles on the liposome solution. This is particularly useful when the material being incorporated is hydrophilic in nature.

Unentrapped biologically active substances can be removed by several means, including repeated centrifugation, decantation, gel filtration, and dialysis. The liposomes are then suspended in a buffer solution. The buffer solution has a pH preferably between pH 4.5 and pH 9.5, more preferably at physiological pH.

Another method of entrapping the substance in a liposome is where the liposomes are formed, in the presence of cholesterol or other adjuvants, if desired, before adding the material to be encapsulated. After the formation is complete, the liposomes are added to an aqueous solution of the material. The solution should be aqueous, although it can include small amounts of organic solvent. The solution is sonicated, and the sonication results in entrapment of the substance inside the liposome.

Another method for entrapping biologically active substances in liposomes is to dissolve the partially formed liposomes or mixture of partially formed liposomes with cholesterol or other adjuvants, as desired, in a suitable organic solvent, such as tetrahydrofuran, acetone, ether, chloroform, methylene dichloride, and ethyl acetate, and evaporate the solvent to form a thin film of partially formed liposomes. Hydrophobic materials are preferably encapsulated in the liposomes by dissolving the materials in an organic solvent with the phospholipid, before forming the liposomes. Hydrophilic materials are more preferably incorporated by hydrating a thin film of liposomes in the presence of an aqueous solution of the substance.

Materials can be entrapped within the liposomes, as well as or alternatively in one or more of the lipid layers of the phospholipid bilayer. This is typically determined by the hydrophobicity/hydrophilicity of the material to be incorporated as well as the method of preparation.

The liposomes can be loaded with up to 100% of the drug to be delivered when the drug is hydrophobic and can be incorporated within the phospholipid bilayer. In general, about 5-40% of the drug is encapsulated when the material is hydrophilic. In one embodiment, the drug is encapsulated during the formation of the liposome. In another embodiment, the liposome is prepared first, and the drug is later entrapped.

In certain other embodiments, the prophylactic or therapeutic agent of choice can be incorporated into liposomes by driving an ionizable drug into the liposome by means of an inside/outside ion gradient across the liposome bilayer, termed remote loading. In a remote loading procedure, a drug is accumulated in the liposomes' central compartment at concentration levels much greater than can be achieved with other loading methods.

Liposomes having an ion gradient across the liposome bilayer for use in remote loading can be prepared by a variety of techniques. A typical procedure is as described above, where a mixture of liposome-forming lipids is dissolved in a suitable organic solvent and evaporated in a vessel to form a thin film. The film is then covered with an aqueous medium containing the solute species that will form the aqueous phase in the liposome interior space. The solute species is then removed from the exterior of the liposome by standard techniques, and the drug is added to the exterior of the liposome for remote loading.

After liposome formation, the vesicles may be sized to achieve a size distribution of liposomes within a selected range, according to known methods. The liposomes are preferably uniformly sized to a selected size range between 0.04 to 0.25 microns.

SUVs, typically in the 0.04 to 0.08 microns range, can be prepared by extensive sonication or homogenization of the liposomes. Homogeneously sized liposomes having sizes in a selected range between about 0.08 to 0.4 microns can be produced, e.g., by extrusion through polycarbonate membranes or other defined pore size membranes having selected uniform pore sizes ranging from 0.03 to 0.5 microns, typically, 0.05, 0.08, 0.1, or 0.2 microns. The pore size of the membrane corresponds roughly to the largest size of liposomes produced by extrusion through that membrane, particularly where the preparation is extruded two or more times through the same membrane. The sizing is preferably carried out in the original lipid hydrating buffer, so that the liposome interior spaces retain this medium throughout the initial liposome processing steps.

After sizing, the external medium of the liposomes is treated to produce an ion gradient across the liposome membrane, which is typically a higher inside lower outside concentration gradient. This may be done in a variety of ways, e.g., by (1) diluting the external medium, (ii) dialysis against the desired final medium, (iii) molecular sieve chromatography, e.g., using Sephadex G-50, against the desired medium, or (iv) highspeed centrifugation and resuspension of pelleted liposomes in the desired final medium. The external medium which is selected will depend on the mechanism of gradient formation and the external pH desired, as will now be considered. For large scale production of liposome, French press or microfluidizer may be used.

In the simplest approach for generating an ion gradient, the hydrated, sized liposomes have a selected internal-medium pH. The suspension of the liposomes is titrated until a desired final pH is reached, or treated as above to exchange the external phase buffer with one having the desired external pH. For example, the original medium may have a pH of 5.5, in a selected buffer, e.g., citrate buffer or ammonium sulfate buffer, and the final external medium may have a pH of 8.5 in the same or different buffer. The internal and external media are preferably selected to contain about the same osmolarity, e.g., by suitable adjustment of the concentration of buffer, salt, or low molecular weight solute, such as sucrose.

In another general approach, the gradient is produced by including in the liposomes, a selected ionophore. To illustrate, liposomes prepared to contain valinomycin in the liposome bilayer are prepared in a potassium buffer, sized, then exchanged with a sodium buffer, creating a potassium inside/sodium outside gradient. Movement of potassium ions in an inside-to-outside direction in turn generates a lower inside higher outside pH gradient, presumably due to movement of protons into the liposomes in response to the net electronegative charge across the liposome membranes (Deamer, et al., 1972).

In another more preferred approach, the proton gradient used for drug loading is produced by creating an ammonium ion gradient across the liposome membrane, as described, for example, in U.S. Pat. No. 5,192,349. Here the liposomes are prepared in an aqueous buffer containing an ammonium salt, typically 0.1 to 0.3M ammonium salt, such as ammonium sulfate, at a suitable pH, e.g., 5.5 to 7.5. The gradient can also be produced by using sulfated polymers, such as dextran ammonium sulfate or heparin sulfate. After liposome formation and sizing, the external medium is exchanged for one lacking ammonium ions, e.g., the same buffer but one in which ammonium sulfate is replaced by NaCl or a sugar that gives the same osmolarity inside and outside of the liposomes.

After liposome formation, the ammonium ions inside the liposomes are in equilibrium with ammonia and protons. Ammonia is able to penetrate the liposome bilayer and escape from the liposome interior. Escape of ammonia continuously shifts the equilibrium within the liposome toward the right, to production of protons.

The therapeutic agent is loaded into the liposomes by adding the drug to a suspension of the ion gradient liposomes, and the suspension is treated under conditions effective to allow passage of the compound from the external medium into the liposomes. Incubation conditions suitable for drug loading are those which (i) allow diffusion of the derivatized compound, with such in an uncharged form, into the liposomes, and (ii) preferably lead to high drug loading efficiencies, e.g., 75 to 100% of drug encapsulated. In one embodiment, 5-500 mM doxorubicin is encapsulated, more preferably between 20-200 mM, most preferably between 50-300 mM.

The loading is preferably carried out at a temperature above the phase transition temperature of the liposome lipids. Thus, for liposomes formed predominantly of saturated phospholipids, the loading temperature may be as high as 60° C. or more. The loading period is typically between 15-120 minutes, depending on permeability of the drug to the liposome bilayer membrane, temperature, and the relative concentrations of liposome lipid and drug.

With proper selection of liposome concentration, external concentration of added compound, and the ion gradient, essentially all of the compound may be loaded into the liposomes. For example, with a pH gradient of 3 units (or the potential of such a gradient employing an ammonium ion gradient), the final internal:external concentration of drug will be about 1000:1. Knowing the calculated internal liposome volume, and the maximum concentration of loaded chug, one can then select an amount of drug in the external medium which leads to substantially complete loading into the liposomes.

Alternatively, if drug loading is not effective to substantially deplete the external medium of free drug, the liposome suspension may be treated, following drug loading, to remove non-encapsulated drug. Free drug can be removed, for example, by molecular sieve chromatography, dialysis, or centrifugation In another embodiment of the invention, the therapeutic agent is loaded into preformed liposomes that include in the liposome interior a trapping agent effective to complex with the therapeutic agent and lead to retention of the compound. In a preferred embodiment, the trapping agent is a polyanionic polymer, e.g., a molecule consisting of repetitive units of preferably similar chemical structure and having ionizable groups, that is, chemical functional groups capable of electrolytic dissociation resulting in the formation of ionic charge, and preferably an anionic charge. Polymers having a molecular weight over a broad range are suitable, from 400-2,000,000 Daltons.

The polyanionic polymer is entrapped in the liposomes during lipid vesicle formation. Upon loading of a drug into the pre-formed liposomes, the polymer serves to trap or retain the drug within the liposomes. In the studies described herein, dextran sulfate was used as an exemplary polyanionic polymer. Dextran sulfate is a polymer of anhydroglucose with approximately 2.3 sulfate groups per glucosoyl residue. It is composed of approximately 95% alpha-D-1-6) linkages and the remaining (1-3) linkages account for the branching of dextran. The polymer is readily available in molecular weights ranging from 5,000 to 500,000 Daltons. However, other polymers are suitable including sulfated, sulfonated, carboxylated or phosphated hydrophilic polymers. For example, sulfated proteoglycans, such as sulfated heparin, sulfated polysaccharides, such as sulfated cellulose or cellulose derivatives, carrageenan, muein, sulfated polypeptides, such as polylysine with sulfated amine groups, glycopeptides with sulfonate-derivatized saccharide or peptide subunits, and hyaluronic acid. Chondroitin sulfates A, B and C, keratin sulfates, dermatan sulfates are also contemplated. The polymer can also be a neutral polymer modified to include an anionic functional group. For example, amylose, pectin, amylopectin, celluloses, and dextran can be modified to include an anionic subunit. Polymers bearing a sulfur group such as polyvinylsulfate, polyvinylsulfonate polystyrenesulfonate and sulfated rosin gum are also suitable.

In one embodiment, the liposome compositions of the present invention additionally contain stabilizing agents. In a preferred embodiment, stabilizing agents are included in the aqueous interior space of liposomes along with an aqueous soluble biologically active material. The term "stabilizer" or "stabilizing agent" as used herein refers to any agent which protects, preserves or stabilizes the conformational structure of a biologically active material, e.g., alpha-tocopherol, which prevents lipid oxidation. In particular, stabilizing agents include, but are not limited to, polyols with multiple hydroxyl groups, such as trehalose, mannitol, sorbitol, sucrose, and surfactants, such as pluronic F-68 and polyethylene-polypropylene block polymers. Other stabilizing agent include alpha-tocopherol, gelatin, glycine, EDTA, polyethylene glycols, polyvinyl pyrrolidone, and $ZnCl_2$.

Other methods, such as reverse evaporation phase liposome preparation, are also suitable.

5.1.5 Delivery of Therapeutics to a Tumor

The system of the present invention is capable of delivering a therapeutic agent to a tumor cell or a tumor-supporting cell in an increased amount compared to using traditional method of drug delivery. In certain embodiments, the delivery system comprises NGR-containing molecules linked to an encapsulating delivery vehicle, such as a liposome, that comprises a therapeutic agent, and is capable of delivering at least 0.5-2 folds, 2-5 folds, 5-10 folds, 15-20 folds, 20-30 folds, 30-40 folds, 40-50 folds, 50-100 folds more of the therapeutic agent to a targeted cell over a period of time as compared to other non-targeted drug delivery systems as well as targeted drug delivery systems. In specific embodiments, the tumor is exposed to over 2-10%, 10-20%, 20-30% 30-40%, 40-50%, 50-60%, 60-70%, 70-80%, 80-90%, or 90-99% of therapeutic agent over a period of at least 2-5 hours, 5-10 hours, 10-12 hours, 12-24 hours, 24-36 hours, 36-48 hours, 3-5 days, 5-7 days, or 1-3 weeks as compared to other delivery systems. Specifically, other parenteral delivery system. The amount of therapeutic agent present in a tumor cell or tumor-supporting cell may be determined by one skilled in the art or by methods used in Section 6 infra.

5.2 Therapeutic/Prophylactic/Diagnostic Uses

The methods of the invention include any therapeutic, prophylactic or diagnostic application that can benefit a subject. In certain embodiments, the invention is directed to methods for preventing, managing, treating or ameliorating cancer, angiogenesis, inflammation, cardiac conditions, or other diseases or disorders associated with endothelial cell proliferation by administering to a subject an effective amount of one or more disease-targeted drug delivery systems. In certain other embodiments, the invention is directed to methods for diagnosing or monitoring the presence or amount of vascular endothelial cells that, for example, expresses an NGR receptor. Pharmaceutical compositions and kits comprising the delivery systems are also encompassed.

5.2.1 Cancer

Cancers and related disorders that can be treated, prevented or diagnosed by the methods and compositions of the present invention include but are not limited to the following: leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma.

The methods and compositions of the invention are also useful in the treatment, prevention or diagnosis of hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal orignin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosacoma, rhabdomyoscarama, and osteosarcoma; and other tumors, including melanoma, xenoderma pegmentosum, keratoactanthoma, seminoma, thyroid follicular cancer and teratocarcinoma. It is also contemplated that cancers caused by aberrations in apoptosis would also be treated by the methods and compositions of the invention. Such cancers may include but not be limited to follicular lymphomas, carcinomas with p53 mutations, hormone dependent tumors of the breast, prostate and ovary, and precancerous lesions such as familial adenomatous polyposis, and myelodysplastic syndromes.

Additional types of cancer include neoblastoma, myxosarcoma, osteogenic sarcoma, endotheliosarcoma, lymphangioendotheliosarcoma, mesothelioma, synoviona, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, *Medicine,* 2d Ed., J. B. Lippincott Co., Philadelphia and Murphy et al., 1997, *Informed Decisions: The Complete Book of Cancer Diagnosis, Treatment, and Recovery,* Viking Penguin, Penguin Books U.S.A., Inc., United States of America). The tumor may be a solid tumor or a non-solid tumor and may be a primary tumor or a disseminated metastatic (secondary) tumor.

In specific embodiments, malignancy or dysproliferative changes (such as metaplasias and dysplasias), or hyperproliferative disorders, are treated or prevented in the ovary, bladder, breast, colon, lung, skin, pancreas, or uterus.

In preferred embodiments, the cancer is a breast tumor, melanoma, neuroblastoma, kidney cancer, or Kaposi's sarcoma.

5.2.2 Therapeutic/Prophylactic Administration

The invention provides methods of preventing, managing, treating and ameliorating cancer, by administrating to a human or non-human animal an effective amount of a tumor-targeted drug delivery system. The targeted drug delivery systems of the invention may be administered to a subject per se or in the form of a pharmaceutical composition.

The subject is preferably a mammal. The mammal can be a non-primate (e.g., cows, pigs, horses, cats, dogs, rats etc.) or a primate (e.g., monkey and human), most preferably a human. The human may be an adult, juvenile, infant, or fetus.

In certain embodiments, the delivery system is administered to the subject, concurrently with one or more other therapeutic or prophylactic composition useful for the treatment of cancer, angiogenesis, inflammation, a cardiac condition, or a disease or disorders associated with damaged or defective endothelial cells. The term "concurrently" is not limited to the administration at exactly the same time, but rather administration in a sequence and within a time interval such that one or more therapeutic or prophylactic composition comprising the delivery system(s) can act together with another composition to provide an increased benefit than if they were administered otherwise. For example, each prophylactic or therapeutic composition may be administered at the same time or sequentially in any order at different points in time; however, if not administered at the same time, they should be administered sufficiently close in time so as to provide the desired therapeutic or prophylactic effect. Each composition can be administered separately, in any appropriate form and by any suitable route. In other embodiments, the composition is administered before, concurrently or after surgery. Preferably the surgery completely removes localized tumors or reduces the size of large tumors. Surgery can also be done as a preventive measure or to relieve pain. In various embodiments, the prophylactic or therapeutic compositions are administered less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In preferred embodiments, two or more compositions are administered within the same patient visit.

In other embodiments, the prophylactic or therapeutic compositions are administered at about 2 to 4 days apart, at about 4 to 6 days apart, at about 1 week part, at about 1 to 2 weeks apart, or more than 2 weeks apart. In preferred embodiments, the prophylactic or therapeutic compositions are administered in a time frame where both compositions are still active. One skilled in the art would be able to determine such a time frame by determining the half life of the administered compositions.

In certain embodiments, the prophylactic or therapeutic compositions of the invention are cyclically administered to a subject. Cycling therapy involves the administration of a first composition for a period of time, followed by the administration of a second composition and/or third composition for a period of time and repeating this sequential administration. Cycling therapy can reduce the development of resistance to one or more of the therapies, avoid or reduce the side effects of one of the therapies, and/or improves the efficacy of the treatment.

In certain embodiments, prophylactic or therapeutic compositions are administered in a cycle of less than about 3 weeks, about once every two weeks, about once every 10 days or about once every week. One cycle can comprise the administration of a therapeutic or prophylactic composition by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In yet other embodiments, the therapeutic and prophylactic compositions of the invention function as a metronomic dosing regimen, by mimicking continuous infusion of a therapeutic or frequent administration without extended rest periods. Such metronomic administration can involve dosing of a therapeutic at constant intervals without rest periods. The dosing regimens encompass the chronic daily administration of relatively low doses for extended periods of time. In preferred embodiments, the use of lower doses can minimize toxic side effects and eliminate rest periods. In certain embodiments, administration of the therapeutic and prophylactic compositions at weekly or longer intervals lead to chronic low-dose or continuous infusion ranging from about 24 hours to about 2 days, to about 1 week, to about 2 weeks, to about 3 weeks to about 1 month to about 2 months, to about 3 months, to about 4 months, to about 5 months, to about 6 months. The scheduling of such dose regimens can be optimalized by the skilled physician.

The dosage amounts and frequencies of administration provided herein are encompassed by the terms therapeutically effective and prophylactically effective. The dosage and frequency further will typically vary according to factors specific for each patient depending on the specific therapeutic or prophylactic composition administered, the severity and type of disease or disorder, the route of administration, as well as age, body weight, response, and the past medical history of the patient. Suitable regimens can be selected by one skilled in the art by considering such factors as the changes in pharmacokinetics and biodistribution of a therapeutic attendant on its encapsulation in a carrier and by following, for example, dosages reported in the literature and recommended in the *Physician's Desk Reference* (56$^{th}$ ed., 2002), with modifications that allow for changes in the pharmacokinetics and biodistribution that accompany drug encapsulation in a carrier.

In specific embodiments, the therapeutic or prophylactic composition comprising the delivery systems of the present invention is administered in conjunction with an appropriate anti-cancer drug or therapy useful in treating or preventing cancer.

Various delivery systems are known and can be used to administer the therapeutic or prophylactic composition of the present invention, e.g., encapsulation in liposomes, microparticles, microcapsules (see, e.g., Wu and Wu, J. Biol. Chem. 262:4429-4432 (1987)), construction of a nucleic acid as part of a retroviral or other vector, etc. Methods of administering a prophylactic or therapeutic composition of the invention include, but are not limited to, parenteral administration (e.g., intradermal, intramuscular, intraperitoneal, intravenous and subcutaneous), epidural, intrathecal, intracerebral and mucosal (e.g., intranasal). In a specific embodiment, prophylactic or therapeutic composition of the invention are administered intramuscularly, intravenously, or subcutaneously. The prophylactic or therapeutic composition may be administered by any convenient route, for example by infusion or bolus injection, and may be administered together with other biologically active agents. Administration can be systemic or local.

In a specific embodiment, it may be desirable to administer the prophylactic or therapeutic composition of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers.

5.2.3 Other Therapeutic/Prophylactic Agents

According to the invention, therapy by administration of the delivery systems may be combined with the administration of one or more therapies such as, but not limited to, chemotherapies, radiation therapies, hormonal therapies, gene therapies, and/or biological therapies/immunotherapies.

In a specific embodiment, the methods of the invention encompass the administration of one or more angiogenesis inhibitors or angiolytic agents such as but not limited to: Angiostatin (plasminogen fragment); antiangiogenic antithrombin III; Angiozyme; ABT-627; Bay 12-9566; Benefin; Bevacizumab; BMS-275291; cartilage-derived inhibitor (CDI); CAI; CD59 complement fragment; CEP-7055; Col 3; Combretastatin A-4; Endostatin (collagen XVIII fragment); Fibronectin fragment; Gro-beta; Halofuginone; Heparinases; Heparin hexasaccharide fragment; HMV833; Human chorionic gonadotropin (hCG); IM-862; Interferon alpha/beta/gamma; Interferon inducible protein (IP-10); Interleukin-12; Kringle 5 (plasminogen fragment); Marimastat; Metalloproteinase inhibitors (TIMPs); 2-Methoxyestradiol; MMI 270 (CGS 27023A); MoAb IMC-1C11; Neovastat; NM-3; Panzem; PI-88; Placental ribonuclease inhibitor; Plasminogen activator inhibitor; Platelet factor-4 (PF4); Prinomastat; Prolactin 16kD fragment; Proliferin-related protein (PRP); PTK 787/ZK 222594; Retinoids; Solimastat; Squalamine; SS 3304; SU 5416; SU6668; SU11248; Tetrahydrocortisol-S; tetrathiomolybdate; thalidomide; Thrombospondin-1 (TSP-1); TNP-470; Transforming growth factor-beta (TGF-b); Vasculostatin; Vasostatin (calreticulin fragment); ZD6126; ZD 6474; farnesyl transferase inhibitors (FTI); and bisphosphonates.

Additional examples of anti-cancer agents that can be used in the various embodiments of the invention, including pharmaceutical compositions and dosage forms and kits of the invention, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; 1-beta-D-arabinofuranosylcytosine ("AraC"); asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; N-phosphonoacetyl-L-aspartate ("PALA"); pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; topotecan; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytotoxic factor; cytostatin; dacliximab; decitabine; dehydrodidemnin B; deslorelin; dexamethasone; dexifosfamide; dexrazoxane; dexverapamil; diaziquone; didenmin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anti-cancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vincristine, vinxaltine; vitaxin; vorozole; zanoterone; zeniplatin; zilascorb; and zinostatin stimalamer. Preferred additional anti-cancer drugs are 5-fluorouracil and leucovorin. These two agents are particularly useful when used in methods employing thalidomide and a topoisomerase inhibitor.

5.2.4 Therapeutic/Prophylactic Compositions

The tumor-targeted drug delivery system of the invention can be incorporated into a pharmaceutical composition suitable for administration. In one embodiment, the composition comprises at least two different delivery systems, wherein at least one of the delivery systems comprises a different therapeutic agent than another delivery system.

The pharmaceutical compositions may be manufactured by means of conventional mixing, dissolving, granulating, levigating, emulsifying, encapsulating, entrapping or lyophilizing processes. Such compositions typically comprise one or more delivery systems, and optionally a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutically acceptable carriers include water, salt solutions, alcohol, silicone, waxes, petroleum jelly, vegetable oil, peanut oil, soybean oil, mineral oil, sesame oil, polyethylene glycols, propylene glycol, liposomes, sugars, gelatin; lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Supplementary active compounds can also be incorporated into the compositions. In one embodiment, the composition further comprises minor amounts of wetting or emulsifying agents or pH buffering agents, such as hydrochloric acid or sodium hydroxide.

The compositions can take the form of solutions, suspensions, emulsions, tablets, pills, capsules, powders, sustained-release formulations and the like, depending on the intended route of administration. Examples of routes of administration include parenteral, e.g., intra-arterial, intraportal, intramuscular, intravenous, intrathecal, intradermal, subcutaneous, transdermal (topical), transmucosal, intra-articular, intraperitoneal, and intrapleural, as well as intrathecal, intracerebral, inhalation and pulmonary administration. In another aspect, the delivery system and pharmaceutical composition are administered to the subject locally, for example, by injection to a local blood vessel which supplies blood to a particular tumor, organ, tissue, or cell afflicted by disorders or diseases.

For parenteral administrations, the composition comprises one or more of the following components: a sterile diluent such as water for injection, saline solution; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

For injection, the delivery systems may be formulated in aqueous solutions, preferably in physiologically compatible buffers such as Hanks's solution, Ringer's solution, or physiological saline buffer. The solution may contain formulatory agents such as suspending, stabilizing and/or dispersing agents. In a preferred embodiment, the delivery systems are formulated in sterile aqueous solutions.

For intravenous administration, suitable carriers include physiological saline, bacteriostatic water, or phosphate buffered saline (PBS). In all cases, the composition must be sterile and should be fluid to the extent that easy injectability with a syringe. It must be stable under the conditions of manufacture and storage and must be preserved against the contaminating action of microorganisms such as bacteria and fungi. The carrier can be a solvent or dispersion medium containing, for example, water, and suitable mixtures thereof. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition.

For administration by inhalation, the delivery systems may be formulated as an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of gelatin for use in an inhaler or insufflator may be formulated containing a powder mix of the delivery systems and a suitable powder base such as lactose or starch.

As the delivery systems of the invention may contain charged side chains or termini, they may be included in any of the above-described formulations as the free acids or bases or as pharmaceutically acceptable salts. Pharmaceutically acceptable salts are those salts which substantially retain the biologic activity of the free bases and which are prepared by reaction with inorganic acids. Pharmaceutical salts tend to be more soluble in aqueous and other protic solvents than are the corresponding free base forms. In certain embodiments, the compositions can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The compositions of the invention will generally be used in an amount effective to achieve the intended purpose. For use to treat or prevent cancer, an amount of the compositions may be administered to ameliorate or prevent the symptoms associated with the cancer, inhibit or reduce the growth of the tumor cells or tumor-supporting cells, or prolong the survival of the patient being treated. In a specific embodiment, the growth of the tumor cells is reduced by 5%, 10%, 20%, 30%, 40%, 50%, 60%, 70%, 80%, 90%, 95%, 96%, 97%, 98%, 99% or 100%. Determination of a therapeutically effective amount is well within the capabilities of those skilled in the art, especially in light of the detailed disclosure provided herein.

The amount of compositions to be administered may vary. The skilled artisan will appreciate that certain factors may influence the dosage required to effectively treat a subject, including but not limited to the severity of the disease or disorder, previous treatments, the general health and/or age of the subject, if other diseases are present, the manner of administration and the judgment of the prescribing physician. The treatment can be a single treatment or a series of treatments. The therapy may be repeated intermittently while symptoms detectable or even when they are not detectable. It will also be appreciated that the effective dosage of nucleic acid molecule used for treatment may increase or decrease over the course of a particular treatment. Changes in dosage may result and become apparent from the results of diagnostic and monitoring assays as described herein.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans by allowing extrapolation of changes in pharmacokinetics and biodistribution observed in animal models to estimations of human doses.

Initial dosages can also be estimated from in vivo data, e.g., animal models, using techniques that are well known in the art. The dosage of such compositions lies preferably within a range of circulating concentrations that include the $ED_{50}$ with little or no toxicity. One skilled in the art could readily optimize administration to humans based on animal data, keeping in mind that encapsulating drug in a carrier can result in significant changes in the pharmacokinetics and biodistribution of the encapsulated drug.

Dosage amount and interval may be adjusted individually to provide levels of the drug at the disease site which are sufficient to maintain therapeutic effect. Levels in plasma may be measured, for example, by high performance liquid chromatography.

Usual patient dosages for administration by injection range from about 0.01 to 30 mg/kg/day, preferably from about 0.1 to 10 mg/kg/day, more preferably from 0.1 to 1 mg/kg body weight. In preferred embodiments, the dosages for administration range from about 0.005-0.01 mg/kg, 0.01-0.05 mg/kg, 0.05-0.1 mg/kg, 0.1-0.5 mg/kg, 0.5-1 mg/kg, 1-1.5 mg/kg, 1.5-2 mg/kg, 2-4 mg/kg, or 4-10 mg/kg. In preferred embodiments, the frequency for administration is once every week, every 2-4 weeks, 4-6 weeks, or 6-8 weeks. Therapeutically effective serum levels may be achieved by administering multiple doses each day, every week, every 2-4 weeks, 4-6 weeks, or 6-8 weeks. Effective doses may be extrapolated from dose-response curves derived from in vitro or animal model test systems.

In preferred embodiments, the dosages for administering the system of the present invention comprising doxorubicin is 0.1-1 mg/kg, two times a week, or 1-12 mg/kg once a week up to six weeks. In preferred embodiments, the dosages for administering the system of the present invention comprising vincristine is 0.1-1 mg/kg, two times a week, or 1-6 mg/kg once a week up to six weeks.

The routes of administration and dosages described are intended only as a guide since a skilled practitioner will be able to determine readily the optimum route of administration and dosage for any particular patient and condition.

5.2.5 Combination Therapy

The delivery systems and/or pharmaceutical compositions of the invention can administered to a subject, sequentially or simultaneously, with surgery, standard and experimental chemotherapies, hormonal therapies, biological therapies, immunotherapies, radiation therapies, embolization, and/or chemoembolization therapies for the treatment or prevention of cancer.

The delivery systems and/or pharmaceutical compositions of the invention can also be administered to a subject, sequentially or simultaneously, with a further therapeutic agent which may be the same as or different to the therapeutic agent contained within the delivery system. In a preferred embodiment, the other therapeutic agent may be one of the aforementioned anti-cancer, anti-angiogenic, pro-angiogenic, angiolytic or anti-inflammatory agents. In specific embodiments, therapeutic agents may be genetic materials such as nucleic acid molecules, including DNA or RNA, encoding a useful molecule, intended to be inserted into the genome of the human body using viral vectors and non-viral vectors, other nucleic acid molecules may be anti-sense nucleic acid molecules such as DNA, RNA and RNAi.

5.2.6 Demonstration of Therapeutic/Prophylactic Use

The compositions of the invention are preferably tested in vitro, and then in vivo for the desired therapeutic or prophylactic activity, prior to use in humans. For example, in vitro assays to demonstrate the therapeutic or prophylactic utility of a composition include, the effect of a composition on a cell line, particularly one characteristic of a specific type of cancer, or a patient tissue sample. The effect of the composition on the cell line and/or tissue sample can be determined utilizing techniques known to those of skill in the art including, but not limited to, rosette formation assays and cell lysis assays. Specifically, breast cancer cell line, such as MDA-MB-231, lymphoma cell line, such as U937, and colon cancer cell line, such as RKO may be used to assess the therapeutic effects of the targeted therapeutic molecules of the present invention. Techniques known to those skilled in the art can be used for measuring cell activities. For example, cellular proliferation can be assayed by $^3$H-thymidine incorporation assays or Molecular Probe's Live/Dead Cytotoxicity Kit.

Test compositions can be tested for their ability to reduce tumor formation in patients (i.e., animals) suffering from cancer. Test compositions can also be tested for their ability to reduce viral load or bacterial numbers in patients suffering from an infectious disease. Test compositions can also be tested for their ability to alleviate of one or more symptoms associated with cancer or angiogenesis, inflammation, a cardiac condition, or a disease or disorder associated with damaged or defective endothelial cells. Test compositions can also be tested for their ability to repair or remove the cancerous cells or damaged or defective endothelial cells. Further, test compositions can be tested for their ability to increase the survival period of patients suffering from cancer or angiogenesis, inflammation, a cardiac condition, or a disease or disorder associated with damaged or defective endothelial cells. Techniques known to those of skill in the art can be used to analyze test to function of the test compositions in patients.

In various embodiments, within the invention, in vitro assays that can be used to determine whether administration of a specific composition is indicated, include in vitro cell culture assays in which a patient tissue sample is grown in culture, and exposed to or otherwise administered a composition, and the effect of such composition upon the tissue sample is observed. Specifically, cytotoxic effects of the expressed proteins may be assessed by Promega's CellTiter 96Aqueous Cell Proliferation assay and Molecular Probe's Live/Dead Cytotoxicity Kit.

Compositions for use in therapy can be tested in suitable animal model systems prior to testing in humans, including but not limited to rats, mice, chicken, cows, monkeys, rabbits, etc. For in vivo testing, prior to administration to humans, any animal model system known in the art may be used.

5.2.6.1 Toxicity

Preferably, a therapeutically effective dose of the delivery system or pharmaceutical composition described herein will provide therapeutic benefit without causing substantial toxicity.

Toxicity of the proteins described herein can be determined by standard pharmaceutical procedures in cell cultures or experimental animals, e.g., by determining the maximum tolerated dose resulting in no significant levels of a particular side effect in an animal population. The dose ratio between toxic and therapeutic effect is the therapeutic index. Therapeutics which exhibit high therapeutic indices are preferred. The data obtained from these cell culture assays and animal studies can be used in formulating a dosage range that is not toxic for use in human. The dosage of the therapeutics described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: *The Pharmacological Basis of Therapeutics*, Ch. 1, p. 1).

5.2.7 Kits

The invention also provides a pharmaceutical pack or kit comprising one or more containers filled with one or more of the delivery systems of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention also provides kits that can be used in the above methods. In one embodiment, a kit comprises the delivery systems or pharmaceutical compositions in one or more containers.

In certain embodiments, the kits of the invention contain instructions for the use of the system of the present invention for the treatment, prevention or diagnosis of cancer, inflammatory disease, viral infections, microbial infections or cardiovascular diseases.

The invention having been described, the following examples are offered by way of illustration and not limitation.

6. EXAMPLES

Most preclinical studies on tumor angiogenesis and anti-angiogenic or angiolytic therapy usually employ rapidly growing transplantable mouse tumors, or human tumor xenografts, which are grown as a solid, localized tumor in the subcutaneous space. For several reasons this approach almost certainly exaggerates the anti-tumor responses. Principally, in such experimental situations, unlike in the clinic, distant metastases are usually not the focus of the treatment, but it is precisely such secondary tumors which are ultimately responsible for cancer's lethality. For these reasons and to elucidate possible influences of the host microenvironment, angiogenesis-specific studies of tumors in an orthotopic location may more closely mimic human disease. For example, the use of orthotopically transplanted neuroblastoma (NB) tumors may be preferable in a animal model for human neuroblastoma, not only to induce or enhance the incidence of metastases but also because the response of a tumor mass growing ectopically may be abnormal compared with the same tumor growing in a physiologically relevant site (Fidler, I. J. *J Natl Cancer Inst* 87, 1588-92 (1995)). The potency of the NGR-targeted sterically stabilized liposomal doxorubicin (DXR) formulation (NGR-SL[DXR]) was revealed by its ability to control and effectively shrink established orthotopic NB tumors in mice as shown in Pastorino, et al., 2003, Cancer Research 63, 7400-7409, which is incorporated by reference in its entirety. The belief that NGR-SL[DXR] affects tumor growth primarily through an angiolytic mechanism is supported by data showing fewer factor VIII positive blood vessels in orthotopic tumors treated with NGR-SL[DXR] compared to control tumors. This is further supported by the observation of an atypical dose-response effect on established tumors. This observation is consistent with the low-dose, delayed effects on tumors typically seen with other reported anti-angiogenic treatment protocols (Browder, supra); Klement, supra) and suggests that the NGR-SL[DXR] is acting as a sustained release system that mimics conventional metronomic dosing without the requirement for the inconvenience of frequent dosing. Low dose anti-angiogenic therapy is currently being explored as an anti-tumor experimental therapy (Miller, supra). In the orthotopic NB model, it has been shown that targeting the chemotherapeutic agent DXR to tumor vessels makes it possible to combine blood vessel destruction with the conventional anti-tumor actions of drug. These findings are in agreement with previous results showing that in mice bearing human cancer xenografts, an anti-angiogenic approach has proven more efficacious and less toxic than conventional therapy (Arap, W. et. al. *Science* 279, 377-80 (1998); Curnis, F. et al. *Nat Biotechnol* 18, 1185-90 (2000); Ellerby, H. M. et al. *Nat Med* 5, 1032-8 (1999); Zhang, L. et al. *Cancer Res* 62, 2034-42 (2002)). However the targeted liposome approach may have another advantage since NGR-SL[DXR] appeared to escape from the vasculature and be delivered directly to the tumor interstitial space. Delivery of the drug to tumor cells themselves by passive targeting of NGR-SL[DXR] (since the NGR-targeted liposomes are not expected to bind to tumor cells directly) is the mechanism of action of the successful clinical liposomal drug, Doxil®/Caelyx® (Muggia, F. et al. *Eur J Cancer* 37 Suppl 9, Si 5-8 (2001)). This potential for dual action of the NGR-targeted liposomes may result in a higher and more durable anti-cancer effect than a strictly anti-angiogenic approach.

6.1 Methods

6.1.1 Liposome Preparation

Non-targeted sterically stabilized liposomes (SL) and peptide-targeted liposomes (NGR-SL) as well as a control, sham-targeted peptide formulation (ARA-SL) were synthesised from HSPC:CHOL:DSPE-PEG$_{2000}$, 2:1:0.1 molar ratio, and HSPC:CHOL:DSPE-PEG$_{2000}$: maleimido-DSPE-PEG$_{2000}$, 2:1:0.08:0.02 molar ratio, respectively (see Pastorino, F. et al. *Cancer Res* 63, 86-92 (2003)). In some preparations, Cholesteryl-[1,2-[$^3$H](N)]-hexadecyl ether ("[$^3$H]CHE") was added as a non-exchangeable, non metabolizable lipid tracer. After evaporation under nitrogen, dried lipid films were hydrated in 25 mM (4-2-hydroxyethyl-1-piperazineethanesulfonic acid ("HEPES"), 140 mM NaCl buffer (pH 7.4). The hydrated liposomes were sequentially extruded (Lipex Biomembranes Extruder, Vancouver, BC) through a series of polycarbonate filters of pore size ranging from 0.2 µm down to 0.08 µm to produce primarily unilamellar vesicles. Liposomal size was characterised by dynamic light scattering using a Brookhaven BI90 submicron particle size analyser (Brookhaven Instruments Corp., Holtsville, N.Y.).

DXR was loaded into liposomes via an ammonium sulphate gradient, as previously reported (see Pastorino supra.). The loading efficiency of DXR was greater than 95% and liposomes routinely contained DXR at a concentration of 150-180 µg DXR/gmol phospholipid (PL).

In order to enhance the accessibility of NGR peptide when bound to liposomes, and also to permit coupling via a thiol to a maleimido moiety on the liposomes, additional residues were added to the peptide amino terminus to provide the NGR-containing peptide GNGRGGVRSSSRTPSDKYC (SEQ ID NO:6) with a C-terminal Cys (Colombo, G. et al. *J Biol Chem* 277, 47891-7 (2002)). The ARA-containing peptide GARAGGVRSSSRTPSDKYC was used as control. Peptide was conjugated to the external surface of liposomes via coupling to the terminus of the maleimido polyethylene glycol distearoylphosphatidylethanolamine (PEG$_{2000}$-DSPE-MAL) liposome component. This was accomplished by mixing freshly prepared liposomes with an equimolar (with respect to the maleimido coupling group) quantity of peptide at 4° C. for 16 hours under argon followed by a 10-fold excess of 2-mercapethanol for 1 hour to derivatise the remaining maleimido groups. Uncoupled peptides were separated from the liposomes by passing the coupling mixture through a Sepharose CL-4B column in HEPES buffer, pH 7.4. The efficiency of coupling was determined by estimating the amount of liposome-associated peptides using the CBQCA Protein Quantification Kit (Molecular Probes Europe, Leiden, The Netherlands).

6.1.2 Cell Line and Cellular Association Studies

To broadly cover the phenotypes exhibited by neuroblastoma cells in vitro, five human NB cell limes GI-ME-N; GI-LI-N, HTLA-230, IMR-32, and SH-SY5Y were used (Ponzoni, M. et al. *Cancer Res* 55, 853-61 (1995)). The cell lines KS1767 (human Kaposi's sarcoma) and THP-1 (human acute monocytic leukemia) were used in some experiments as controls. All cell lines were grown in RPMI 1640 medium supplemented with 10% foetal bovine serum, as previously described (see Ponzoni, supra.).

The cellular association of liposomes targeted via NGR peptides was analyzed by flow cytometry (FACS), using a FACScan instrument for fluorescence-activated cell sorting (Becton-Dickinson Immunocytometry Systems). Aliquots of cells ($1 \times 10^6$/tube) were incubated for 1 hour at 4° C. with different formulations of free (non-entrapped) DXR or liposome-entrapped DXR (SL[DXR], NGR-SL[DXR] or ARA-SL[DXR]). The cells were subsequently washed with phosphate-buffered saline (PBS), and enumerated by FACS.

Expression of CD13-binding sites by cultured SH-SY5Y, THP-1 and KS1767 cells was also measured by FACS, using 1 μg/ml WM15 antibody (PharMingen, San Diego, Calif.), as reported (Curnis, F. et al. *Cancer Res* 62, 867-74 (2002).

6.1.3 Orthotopic Neuroblastoma Animal Model

Five-week-old female SCID mice were purchased from Harlan Laboratories (Harlan Italy-S. Pietro al Natisone, UD). Mice (6-8 mice/group) were anaesthetised and injected with the different NB cell lines ($2.5 \times 10^6$ cells in 20 μl of HEPES buffer), after laparatomy, in the capsule of the left adrenal gland. The lethality of the method was 0%. Mice were monitored at least two times weekly for evidence of tumor development, tumor size was quantified, and evidence of tumor-associated morbidity was noted. All experiments involving animals have been reviewed and approved by the licensing and ethical committee of the National Cancer Research Institute and by the Italian Ministry of Health.

6.1.4 Biodistribution and Pharmacokinetic Experiments

SCID mice bearing orthotopically implanted NB tumors (mean volume approximately 100 mm$^3$), were injected via the tail vein with a single dose of liposomes (0.5 μmol PL/mouse), with or without NGR peptides coupled to the liposome surface. The liposomes contained approximately $3 \times 10^5$ cpm of the lipid tracer [$^3$H]CHE. At selected time points (2, 12, 24 hours) post-injection, mice (3 mice/group) were anaesthetised and sacrificed by cervical dislocation. A blood sample (100 μl) was collected by heart puncture and counted for the $^3$H label in a Packard beta-counter. Blood correction factors were applied to all samples (see Pastorino supra.). Biodistribution was determined as previously described (Moreira, J. N. et al. *Biochim Biaphys Acta* 1514, 303-17 (2001)). Data were expressed as the percentage of injected dose/g of tissue.

6.1.5 Histological Analysis

Paraffin-embedded tissue sections (5 μm) were examined after visualization with Mayer's Hematoxylin and Eosin stain (Sigma Chemical Co., St. Louis, Mo.). Monoclonal antibodies against the endothelial cell marker, factor VIII (M616, Dako, Glostrup, Denmark) and anti-human NB (NB84a, Dako) were used. Briefly, sections were collected on 3-amino-propyltriethoxysilane-coated slides, de-paraffinised by the xylene-ethanol sequence, re-hydrated in a graded ethanol scale in TRIS-buffered saline (TBS, pH 7.6), and incubated overnight at 4° C. with M616 (1:25 in TBS) or NB84a (1:40), after prior antigen retrieval by enzymatic digestion with Ficin (Sigma). The immunoreaction was performed with the streptavidin-peroxidase complex (LSAB2, Dako), using Fast Red as a chromogen.

TUNEL (i.e., terminal deoxynucleotidyl transferase-mediated end labeling) staining was performed using a commercially available apoptosis detection kit (In situ Cell Death Detection, POD; Roche Molecular Biochemicals, Mannheim, Germany) according to manufacturer's instructions.

6.1.6 Determination of Microvessel Area

Two investigators with a computerized image analysis system (Leica Quantimet 5000, Wetzlar, Germany) simultaneously assessed microvessel area. Four to six 250× magnification fields, covering almost the whole of each 3 sections (every third section within 9 serial sections) per sample, were examined with a 484-intersection-point square reticulum ($12.5 \times 10^2$/mm$^2$) inserted in the eyepiece. Care was taken to select microvessels, i.e., capillaries and small venules, from all the factor VIII-stained vessels. They were identified as transversally sectioned tubes with a single layer of endothelial cells, without or with a lumen (diameter ranging from 3 to 10 μm). Microvessels were counted by a planimetric point-count method with slight modifications, according to which only microvessels transversally cut occupying the reticulum points were counted. Since the microvessel diameter was smaller than the distance between adjacent points, only one transversally sectioned microvessels could occupy a given point. Microvessels transversally sectioned outside the points and those longitudinally or tangentially sectioned were omitted. It was thus sufficiently certain that a given microvessel was counted only once, even in the presence of several of its section planes. As almost the entire section of each of 3 non-adjacent sections was analyzed per sample, and as transversally sectioned microvessels hit the intersection points randomly, the method allowed objective counts.

6.1.7 In vivo Therapeutic Studies $2.5 \times 10^6$ SH-SY5Y cells were injected orthotopically in the left adrenal gland of mice. Tumors were allowed to grow for 21 days and then i.v. DXR treatment (free or encapsulated in targeted or non-targeted liposomes) was initiated every week for 3 weeks with different DXR doses (see Legends and Results). At various time-points, mice were sacrificed and tumors were measured with calipers. Tumor volumes were calculated by the formula $\pi/6 [w_1 \times (w_2)^2]$, where $w_1$ represented the largest tumor diameter and $w_2$ represented the smallest tumor diameter. The body weight and general physical status of the animals were recorded daily and the mice were terminated when tumor reached 1000-1200 mm$^3$. Histological evaluation of microscopic metastases was performed for all tissues. Organs were fixed in neutral buffered 10% formalin, processed by standard methods, embedded in paraffin, sectioned at 5 μm, stained for immunohistochemistry (IHC) and counterstained with Hematoxylin-Eosin. Weight due to tumor burden was calculated by subtracting the normal wet organ weight from each tumor-bearing organ. In some experiments, mice were monitored routinely for weight loss, and survival times were used as the main criterion for determining treatment efficacy. All the in vivo experiments have been performed at least three times with similar results.

6.1.8 Statistical Methods

The statistical significance of differential findings between experimental groups and controls was determined by Student's t-test and considered significant if two-tailed P values were <0.05. Peto's log-rank test determined the significance of the differences between experimental groups in the survival experiments by the use of StatsDirect statistical software (CamCode, Ashwell, UK).

6.2 Results

6.2.1 Characterization of NCR-targeted Liposomes and Binding to Endothelial Cells in vitro Liposomes were typically 90-115 nm in diameter, with a DXR entrapment efficiency in liposomes of approximately 95%. All liposomal formulations showed minimal leakage in PBS, retaining >90% of the encapsulated DXR after a 24 h incubation. As expected from our previous data (Lopez D. M. et al. *J Liposome Res* 9, 199-228 (1999); Pastorino, F. et al. supra.), when leakage experiments were conducted in 25% human plasma, liposomes showed a slow DXR leakage (12%) at 24 h. For the targeting domain, we used the NGR motif which binds a CD13 isoform selectively expressed by tumor-associated vessels (Curnis, F. et al. *Cancer Res* 62, 867-74 (2002)); Colombo, G. et al. *J Biol Chem* 277, 47891-7 (2002)), for which there is evidence of internalization (Arap, supra); Ellerby, H. M. et al. *Nat Med* 5, 1032-8 (1999)). An average coupling efficiency for the NGR peptide of 55% (95% C.I.=50-60%) was obtained, resulting in a peptide density of 7-8 μg peptide/μmol phospholipid.

Figure 1D:
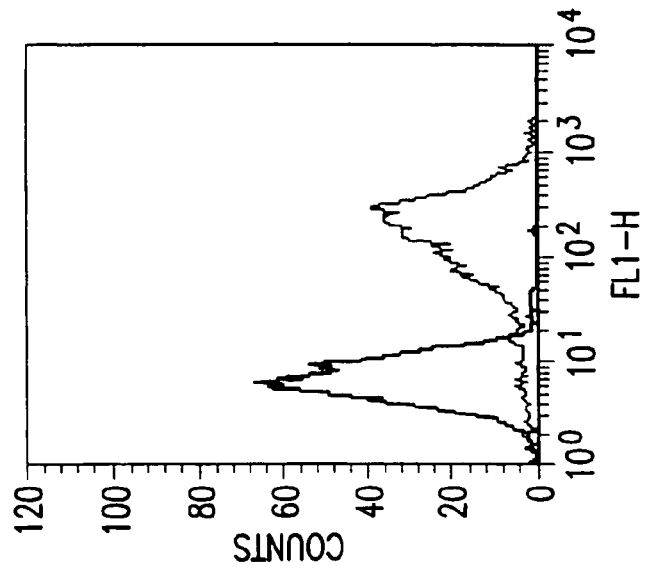

To evaluate the specificity of NGR-targeted liposomal DXR (NGR-SL[DXR]), we used KS1767 cells, derived from Kaposi's sarcoma, because they bind the NGR targeting peptide, as do endothelial cells (Arap, supra); Ellerby, H. M. et al. *Nat Med* 5, 1032-8 (1999)). The THP-1 (acute monocytic leukemia) cell line was used as a control because it does not bind the NGR peptide (Curnis, F. et al *Cancer Res* 62, 867-74 (2002)). FACS analysis showed that WM15 (a monoclonal antibody specific for CD13) bound to both THP-1 and KS1767 cells (FIGS. 1*a* and 1*d*, respectively). In contrast, NGR-SL[DXR] were able to bind the KS1767 cells (FIG. 1*e* and inset), but not the THP-1 cells (FIG. 1*b* and inset), thus confirming pervious results indicating the existence of different isoforms within the CD13 molecule (Curnis, F. et al *Cancer Res* 62, 867-74(2002)). Of note, neither WM-15 nor NGR-SL[DXR] bound to SH-SY5Y NB cells (FIGS. 1*g* and 1*h*). To further confirm the selectivity of binding of our liposomal formulation, we used the mismatched peptide ARA as a targeting moiety. In this case, ARA-SL[DXR] did not bind to any cell lines (FIGS. 1*c*, 1*f* and 1*i*).

6.2.2 Biologically Relevant Orthotopic Neuroblastoma Xenograft Model

A more realistic view of the clinical potential of NGR-targeted liposomes in the treatment of neurblastoma could be obtained if a tumor model were available that better reflected the growth of advanced NB in children (i.e., large adrenal gland tumors and multiple small metastatic lesions). All current data support this concept and recommend that orthotopic implantation of tumor cells in recipient animals is mandatory for studies of tumor progression, angiogenesis, invasion, and metastasis (Chambers, A. F. et al. *Nat Rev Cancer* 2, 563-72 (2002)).

Figure 2A:
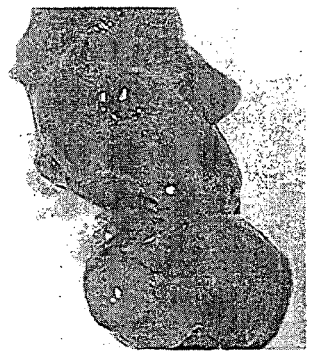
Figure 2B:
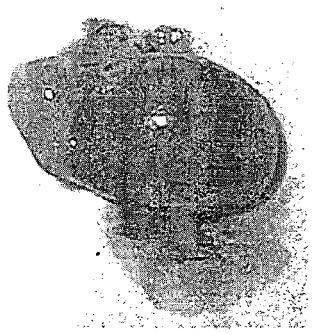
Figure 2C:
Figure 2D:
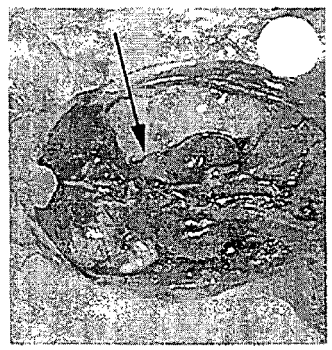
Figure 2E:
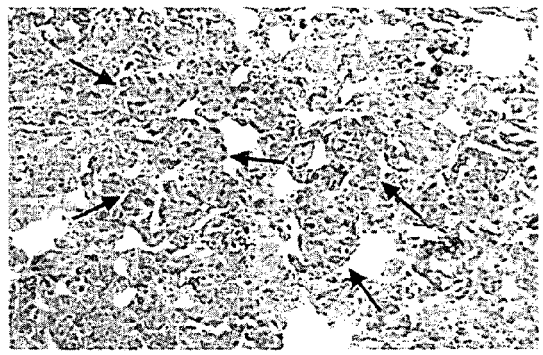
Figure 2F:
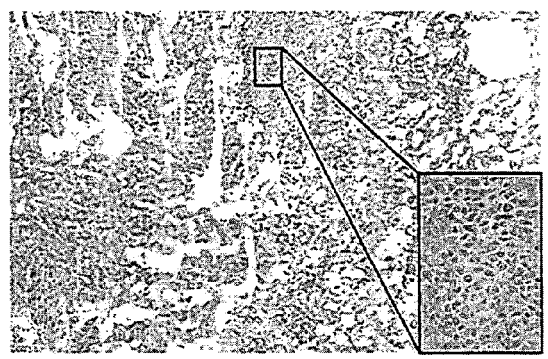
Figure 2G:
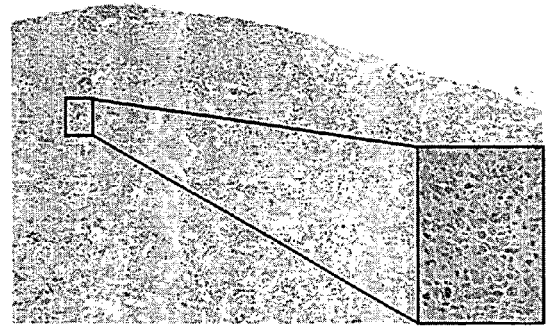
Figure 2H:
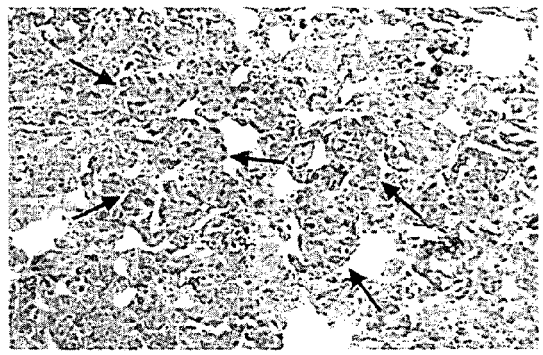

In order to provide a well characterised, relevant, highly reproducible, angiogenic, and metastatic orthotopic model of NB, studies were initiated to define five adrenal NB xenograft models, based on previously described human NB Cell lines (Ponzoni, supra) and reported animal models (Engler, S. et al. *Cancer Res* 61, 2968-73 (2001); Khanna, C. et al. *In Vivo* 16, 77-85 (2002)). From these data (not shown), it was decided to use the intra-adrenal injection of SH-SY5Y cells in mice for further studies, because, 2-3 weeks after injection, adrenal gland tumors were always found in all animals (FIG. 2*a*). This model best reflected the typical growth pattern of human NB, since orthotopic injection of SH-SY5Y cells resulted in solid adrenal tumors that were highly vascular, locally invasive into surrounding tissues, and metastatic to distant sites. Indeed, macroscopic metastases always occurred at 3-4 weeks post-injection in the contralateral adrenal (FIGS. 2*b* and 2*c*) and liver (FIG. 2*d*), while micrometastases were frequently apparent in the ovary (FIG. 2*f*), right kidney (FIG. 2*g*), liver (FIG. 2*h*), and lung (FIG. 2*i*).

Figure 3D:
Figure 3G:
Figure 3C:
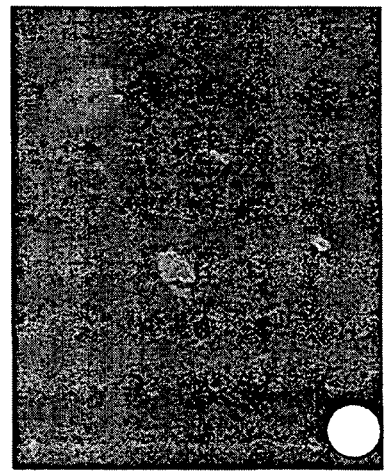
Figure 3F:
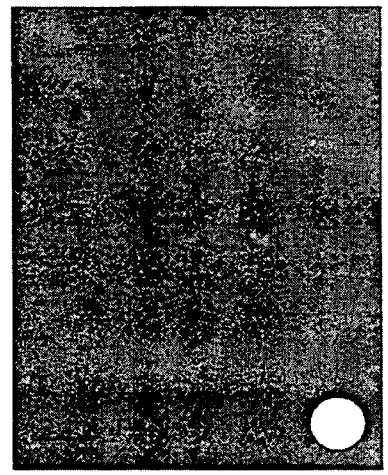

6.2.3 Pharmacokinetic and Biodistribution Profiles of NGR-targeted Liposomes As previously shown (Gabizon, A. et al. *Cancer Res* 54, 987-92 (1994)), long circulation times are requited for small liposomes to gain access to solid tumor sites. Thus, the pharmacokinetics (PK) and biodistribution (BD) of [$^3$H]-CHE-labeled SL and NGR-SL was evaluated in xenograft models of orthotopic NB in SCID mice. The results of the PK studies are expressed as percentage of the administered dose of lipid remaining in blood. These findings clearly indicate that liposomes coupled to NGR peptide had long-circulating profiles in blood, being almost identical to that obtained with non-targeted SL (FIG. 3*a*). The BD of liposomes was evaluated at 2, 12 and 24 h post-injection. At all times, the spleen uptake of targeted liposomes was approximately 10-20 times higher than that of SL. No differences between uptake of SL versus NGR-SL occurred in other tissues, and, with the exception of liver, uptake into other organs was very low (Table 1—below). Tumor accumulation of targeted and non-targeted liposomes was also evaluated. The uptake into tumor by NGR-SL was time-dependent, being at least 10-20 times higher than that of SL after 24 hours (FIG. 3*b*). No uptake was observed into tumors of mice treated with ARA-SL (FIGS. 3*b* and 3*f*).

TABLE 1

Tissue distributions of NGR-targeted or non-targeted liposomes in SCID mice.

| Time | Lung | Heart | Spleen | Liver | Kidney | Brain |
|---|---|---|---|---|---|---|
| | | | % of injected dose | | | |
| NGR-³H-SL[DXR] | | | | | | |
| 2 h | 1.3 ± 0.6 | 0.00 | 25.9 ± 5.1 | 11.11 ± 4.19 | 0.38 ± 0.03 | 0.00 |
| 12 h | 0.9 ± 0.1 | 0.01 ± 0.01 | 48.4 ± 0.1 | 23.52 ± 2.18 | 0.43 ± 0.10 | 0.00 |
| 24 h | 0.9 ± 0.12 | 0.05 ± 0.03 | 55.4 ± 3.2 | 22.41 ± 5.92 | 0.68 ± 0.12 | 0.00 |
| ³H-SL[DXR] | | | | | | |
| 2 h | 0.12 ± 0.01 | 0.02 ± 0.03 | 0.32 ± 0.26 | 3.96 ± 1.84 | 0.90 ± 0.17 | 0.00 |
| 12 h | 0.09 ± 0.01 | 0.03 ± 0.01 | 2.64 ± 0.15 | 22.78 ± 0.62 | 1.10 ± 0.96 | 0.00 |
| 24 h | 0.08 ± 0.01 | 0.12 ± 0.06 | 4.15 ± 0.26 | 29.25 ± 0.99 | 1.91 ± 0.4 | 0.00 |

6.2.4 Homing to Tumor Vasculature

To determine whether the NGR-targeted liposomes could deliver DXR to angiogenic tumor-associated blood vessels, NGR-SL[DXR] was injected into the tail vein of mice bearing established adrenal tumors. In one set of experiments, liposomes were allowed to circulate from 2 to 24 h, followed by perfusion and immediate tissue recovery. There was a clear time-dependent uptake of DXR in the tumor vasculature (FIGS. 3c, 3d and 3e). At 24 h, the staining pattern indicated that the DXR had spread outside the blood vessels and into the tumors. This spreading may be attributable to increased permeability of tumor blood vessels to the intact liposomes (Jain, R. K. *Science* 271, 1079-80 (1996)) or uptake of the targeted liposomes by angiogenic endothelial cells and subsequent transfer to tumor cells, as shown for the uptake of phage (Arap, supra). It is likely that both mechanisms are working at the same time. In the second set of experiments, tissues were examined 16 h after the injection of NGR-SL[DXR] or ARA-SL[DXR]. Strong DXR staining in tumor vasculature was seen only in animals treated with NGR-liposomes (FIG. 3g vs. FIG. 3f). At this time, minimal DXR staining was observed in the spleen and liver, and no detectable expression was found in the heart, lung, kidney, and brain (data not shown.). Tumor-specific DXR uptake was completely blocked when mice were co-injected with a 50-fold molar excess of the soluble NGR peptide (FIG. 3h).

6.2.5 In vivo Therapeutic Studies

To determine whether liposomes homing to the tumor vasculature could be used to improve the therapeutic index of the chemotherapeutic agent DXR, SH-SY5Y cells were injected into the left adrenal gland of SCID mice and allowed to grow for 21 days, at which time they reached a size of approximately 200 mm³. The commonly used dose of DXR in SCID mice with human tumor xenografts is 1-3 mg/kg/week for 3-4 weeks (Moase, E. H. et at. *Biochim Biophys Acta* 1510, 43-55 (2001); Zhang, supra. Because the liposomal DXR was expected to be more effective and less toxic than the free drug, we initially performed a dose-escalation experiment in which mice with established tumors were treated with different doses of DXR once a week for 3 weeks and then observed for an extended period of time. Tumor-bearing mice treated with 2 mg/kg/week outlived the control mice, all of which died from widespread disease (FIG. 4a, Log Rank test, P<0.001 and FIGS. 4b, 4c and 4d). However, higher doses were toxic, since all of the mice treated three times daily with 4 and 8 mg/kg/week died within 48 hours of the third and second drug administration, respectively. Thus, the maximum tolerated total dose (MTD) of targeted liposomal DXR in SCID mice, for this dosing schedule was between 6 and 12 mg.

To assess the impact of NGR-SL[DXR] on tumor cell viability, cryosections taken from tumors at 24 h after the third treatment were stained and examined at low and medium magnification to evaluate both blood vessels and surrounding tumor parenchyma. Histopathological analysis of excised tumor on day 36 revealed pronounced destruction of the tumor vasculature with a marked decreased in vessel density following treatment of the mice with 2 mg/kg/week×3 of NGR-SL[DXR] (FIG. 4g). Double staining of tumors with TUNEL and anti-factor VIII antibody or anti-human NB, demonstrated endothelial cell apoptosis in the vasculature (FIG. 4i) as well as increased tumor cell apoptosis (FIG. 4o), respectively. Interestingly, apoptosis induced by NGR-SL [DXR] was prominent only in the tumor tissues; similar treatment resulted in no observable apoptosis in normal tissue such as heart, lung, kidneys, liver, and spleen (data not shown).

To further test the therapeutic efficacy of this treatment, we randomly sorted mice bearing established 200 mm³ SH-SY5Y adrenal tumors into three groups and treated each group with a weekly tail vein injection of HEPES buffer (untreated controls) or 3 mg/kg DXR entrapped in NGR-SL or in ARA-SL for 3 consecutive weeks. Mice injected with HEPES buffer or ARA-SL[DXR] formed large tumors (1100-1200 mm³) and, consequently, were euthanised on day 42 (FIG. 5a). In contrast, mice injected with NGR-SL[DXR] displayed rapid tumor regression (FIG. 5a). One day after the third treatment, four of six mice showed no evidence of tumors, and the two others showed a >80% reduction in tumor mass and a >90% suppression of blood vessel density (FIG. 5a inset; P<0.01). These findings demonstrated that aminopeptidase N-targeting delivery of DXR to blood vessels caused tumor regression because of its ability to promote apoptosis of the angiogenic endothelium.

Figure 5B:
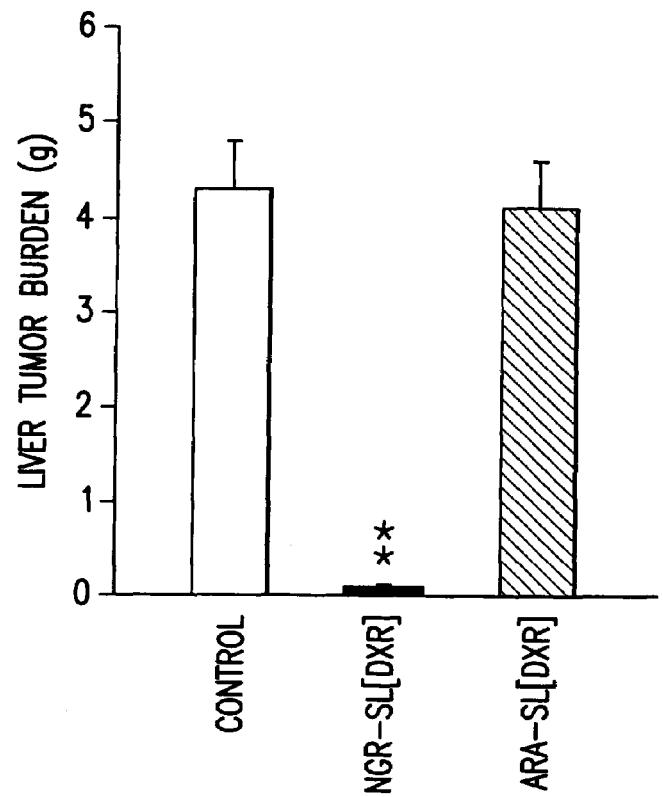
Figure 5C:
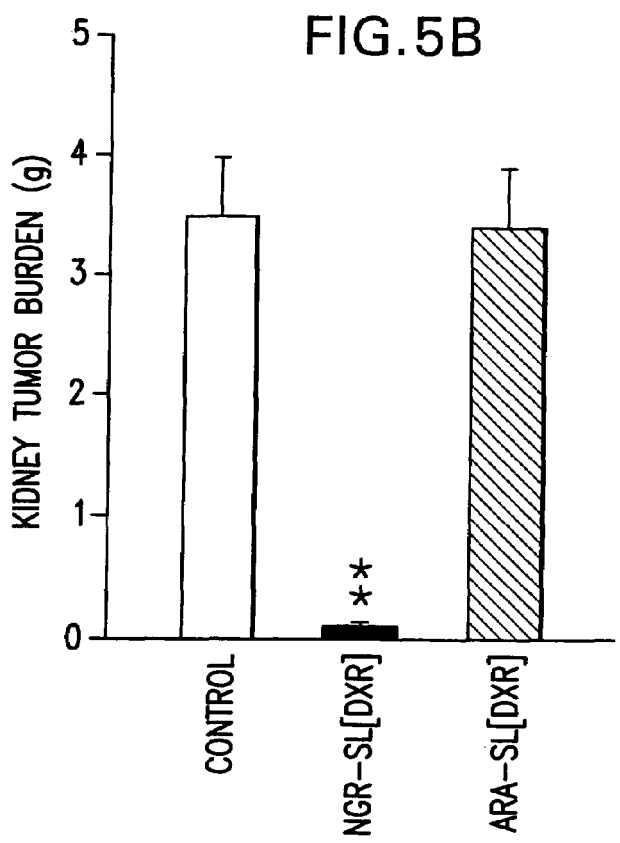

The effect of this therapy against established metastases was also examined. Control mice treated with HEPES buffer or ARA-SL[DXR] showed extensive tumor burdens in the liver and right kidney (FIGS. 5b and 5c). In contrast, mice treated with NGR-SL[DXR] displayed little or no visible tumor metastasis, as demonstrated by a significant reduction in wet liver or kidney weight (FIGS. 5b and 5c; P<0.01).

Figure 5D:
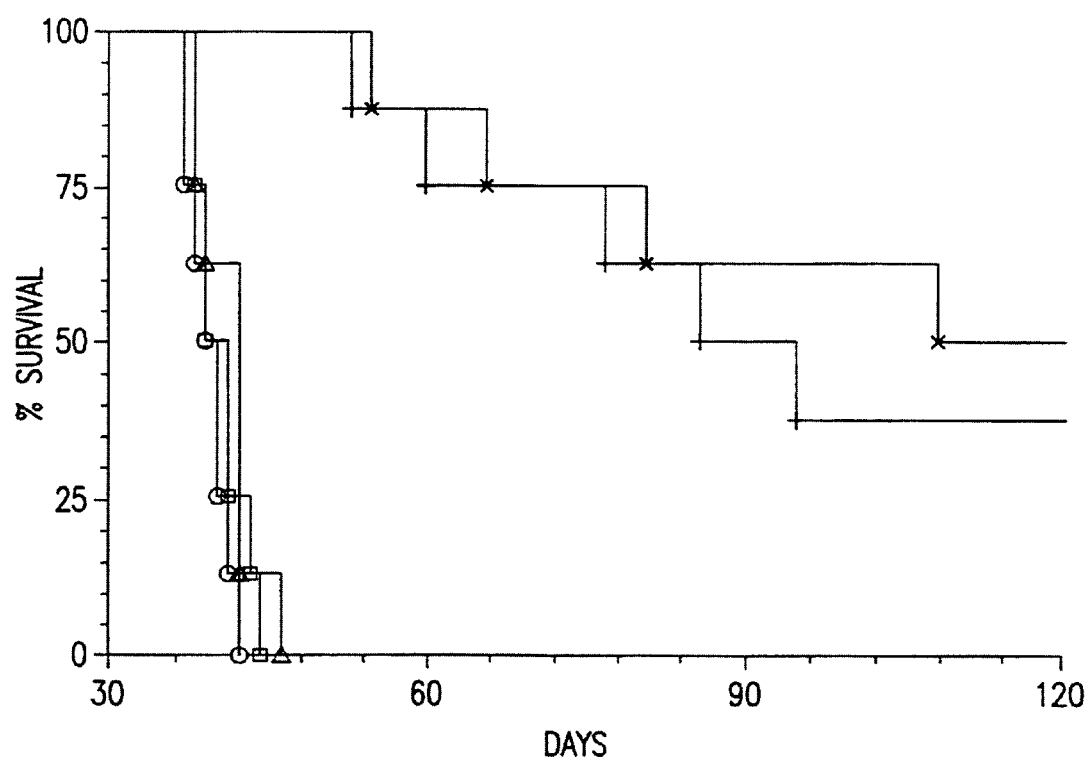

Finally, to test whether the NGR-SL[DXR] were functioning as a sustained release system that mimicked a continuous low-dose administration of chemotherapy agents (an anti-angiogenic schedule of chemotherapy) (Browder, supra; Klement, supra), standard dosing schedule of 3 mg/kg/wk×3 was compared with a more frequent, lower dose administration of DXR, either free or encapsulated into NGR-targeted liposomes (1 mg/kg/every two days×9). The tumor shrank to undetectable levels in all animals treated with liposomal DXR given by either schedule and the observed tumor growth inhibition was maintained beyond four months in four of 8 mice and in three of 8 mice treated with the lower dose, more frequent or the higher dose, less frequent schedules, respectively. As would be expected for a sustained release formulations, no significant differences occurred between either liposomal drug schedule. However, the NGR-SL[DXR] liposomes showed a significant improvement (P<0.0001, and P=0.0002, respectively) in long-term survival (LTS) compared with control animals or mice treated with free DXR, given either by a standard or by a metronomic schedule (FIG. 5d). Indeed, in light of the lack of therapeutic effect of standard or metronomic dosing of free DXR and the exceedingly modest effects of the non-targeted SL[DXR] the therapeutic improvement in animals treated with NGR-SL[DXR] treatment was both dramatic and unexpected.

6.3 DISCUSSION

Although NGR-targeted liposomes are not expected to bind to the tumor cells (which lack CD13 receptors), they passively targeted to the tumor interstitial space. It is likely that increased passive targeting occurs for the NGR-SL[DXR] as they begin to kill the tumor vasculature endothelial cells, which leads to increases in the vascular permeability of the tumor. The inventors believe that this passive targeting of NGR-liposomes results in direct tumor cell kill, including cytotoxicity against cells that are at the tumor periphery and are independent of the tumor vasculature. These vasculature-independent cells can be responsible for disease relapse following anti-angiogenic therapy (Huang, supra.)

The results above show that NGR-targeted liposomal DXR selectively interacts with tumor vasculature. Different CD13 isoforms exist and the NGR domain selectively recognize a CD13 isoform associated with tumor vessels (Curnis, F. et al., *J Clin Invest* 110, 475-82 (2002)). It is believed that NGR-targeted liposomes rapidly interact with CD13-positive endothelial cells because of high-avidity multivalent binding, and that they interact little or not at all with CD13-negative endothelial cells of normal vessels, because of lower avidity, confirming previous finding obtained with the construct NGR-Tumor Necrosis Factor (Curnis, F. et al. *J Clin Invest* 110, 475-82 (2002)). The present invention showed that treatment with NGR-targeted liposomal formulations of DXR inhibited vascularisation and, hence, reduced total tumor volume and weight. IHC analysis of the orthotopic neuroblastoma tumors demonstrated a significant decrease in microvessel density with an associated increase in apoptosis of tumor cells and tumor-associated endothelial cells. Indeed, double staining of endothelial cells with antibodies against factor VIII and TUNEL suggested that the reduction in microvessel density was attributable to a pronounced increase of apoptosis in the endothelial cells. The appearance of significant quantities of DXR associated with tumor cells, as well as tumor endothelial cells suggests that destruction of the tumor endothelial cells was increasing vascular permeability, which, in turn, allowed more NGR-SL[DXR] to extravasate (i.e., passively target) into the tumor intrastitial space, leading to direct tumor cell kill.

Although studies have been performed in a mouse model, it is expected that the NGR motif will target human vasculature as well, because the NGR phage has been shown to bind to blood vessels of human tumors (Arap, supra). Thus, this peptide is potentially suitable for tumor targeting in patients. The invention may also be used with other targeting domains which target vasculature.

In conclusion, the targeting of the vasculature of diseased organs could be the basis of a new pharmacological approach for the treatment of malignancies. This treatment takes advantage of formulations that delivery cytotoxic drugs in a metronomic manner to both blood vessels located specifically at sites of disease and to the tumor cells themselves. This should improve efficacy and reduce side effects. The approach may also be used in the treatment of conditions requiring the delivery of angiogenic, angiolytic and anti-angiogenic agents, including inflammatory conditions.

7. EQUIVALENTS

Those skilled in the art will recognize, or be able to ascertain using no more than routine experimentation, many equivalents to the specific embodiments of the invention described herein. Such equivalents are intended to be encompassed by the following claims. Furthermore, the principle of the present invention is not limited to any following independent or dependent claims, which are specific embodiments of the invention.

All publications, patents and patent applications mentioned in this specification are herein incorporated by reference into the specification to the same extent as if each individual publication, patent or patent application was specifically and individually indicated to be incorporated herein by reference.

Citation or discussion of a reference herein shall not be construed as an admission that such is prior art to the present invention.

---

SEQUENCE LISTING

```
<160> NUMBER OF SEQ ID NOS: 7

<210> SEQ ID NO 1
<211> LENGTH: 6
<212> TYPE: PRT
<213> ORGANISM: Homo sapiens

<400> SEQUENCE: 1

Asn Gly Arg Ala His Ala
1               5
```

```
<210> SEQ ID NO 2
<211> LENGTH: 5
<212> TYPE: PRT
<213> ORGANISM: Homo sapiens

<400> SEQUENCE: 2

Gly Asn Gly Arg Gly
 1               5

<210> SEQ ID NO 3
<211> LENGTH: 5
<212> TYPE: PRT
<213> ORGANISM: Homo sapiens

<400> SEQUENCE: 3

Cys Asn Gly Arg Cys
 1               5

<210> SEQ ID NO 4
<211> LENGTH: 13
<212> TYPE: PRT
<213> ORGANISM: Homo sapiens

<400> SEQUENCE: 4

Cys Asn Gly Arg Cys Val Ser Gly Cys Ala Gly Arg Cys
 1               5                  10

<210> SEQ ID NO 5
<211> LENGTH: 9
<212> TYPE: PRT
<213> ORGANISM: Homo sapiens

<400> SEQUENCE: 5

Cys Val Leu Asn Gly Arg Met Glu Cys
 1               5

<210> SEQ ID NO 6
<211> LENGTH: 19
<212> TYPE: PRT
<213> ORGANISM: Homo sapiens

<400> SEQUENCE: 6

Gly Asn Gly Arg Gly Gly Val Arg Ser Ser Ser Arg Thr Pro Ser Asp
 1               5                  10                  15

Lys Tyr Cys

<210> SEQ ID NO 7
<211> LENGTH: 10
<212> TYPE: PRT
<213> ORGANISM: Homo sapiens

<400> SEQUENCE: 7

Val Arg Ser Ser Ser Arg Thr Pro Ser Asp
 1               5                  10
```

What is claimed:

1. A tumor-targeted drug delivery composition comprising an NGR-containing molecule, wherein said NGR-containing molecule comprises an NGR amino acid sequence motif and a TNF amino terminal sequence, wherein said TNF amino terminal sequence consists of an amino acid sequence of SEQ ID NO: 7, and wherein said NGR-containing molecule is covalently attached to an encapsulating delivery vehicle, wherein said encapsulating delivery vehicle comprises a therapeutic agent.

2. The delivery composition of claim 1, wherein the NGR amino acid sequence motif comprises the amino acid sequence of SEQ ID NO:1, SEQ ID NO:2, SEQ ID NO:3, SEQ ID NO:4, SEQ ID NO:5, or SEQ ID NO:8.

3. The delivery composition of claim 1, wherein the tumor is a breast tumor, lung tumor, colon cancer, melanoma, neuroblastoma, Kaposi's sarcoma, kidney tumor, or ovarian tumor.

4. The delivery composition of claim 1, wherein the delivery vehicle is a liposome, micelle, lipidic micelle, microsphere, nanosphere, chambered microdevice, emulsion, lipid disc, polymer, cell, viral particle, or virus.

5. The delivery composition of claim 4, wherein the liposome comprises amino-polyethylene glycol phosphatidylethanolamine, methoxy-polyethylene glycol phosphatidylethanolamine, maleimido-polyethylene glycol phosphatidylethanolamine, N-methylpalmitoyloleoylphosphatidylcholine, phosphatidylserine, hydrogenated soy phosphatidylcholine, sphingomyelin, phosphatidylglycerol, palmitoyloleoylphosphatidylcholine, dipalmitoylphosphatidylcholine, distearoylphosphatidylcholine, diphytanoylphosphatidylcholine, sphingomyelin, cholesterol, derivatives thereof, or a combination thereof.

6. The delivery composition of claim 1, wherein the NGR-containing molecule is attached to the encapsulating delivery vehicle through a linking agent.

7. The delivery composition of claim 1, wherein the therapeutic agent is an anti-inflammatory drug, an anti-angiogenic drug, a pro-angiogenic drug, or an angiolytic drug.

8. The delivery composition of claim 1, wherein the therapeutic agent is a cytotoxic agent.

9. The delivery composition of claim 1, wherein the therapeutic agent is a cancer chemotherapeutic agent.

10. The delivery composition of claim 1, wherein the therapeutic agent is an oligonucleotide.

11. The delivery composition of claim 9, wherein the cancer chemotherapeutic agent is a microtubule inhibitor.

12. The delivery composition of claim 9, wherein the cancer chemotherapeutic agent is doxorubicin, vincristine, mitoxantrone, calicheamicin, Iressa or Gleevec.

13. A pharmaceutical composition comprising the delivery composition of claim 1 and a pharmaceutically acceptable excipient.

14. The tumor-targeted drug delivery composition of claim 1, wherein the NGR-containing molecule comprises the amino acid sequence of SEQ ID NO: 6 linked to a liposome via a thiol to a maleimido moiety on the liposome, and wherein said therapeutic agent comprises doxorubicin.

15. The delivery composition of claim 6, wherein the linking agent is polyethylene glycol (PEG).

16. A tumor-targeted delivery composition comprising an NGR-containing molecule linked to an encapsulating delivery vehicle, said NGR-containing molecule consisting of the amino acid sequence of SEQ ID NO: 6 or (i) the amino acid sequence selected from the group consisting of SEQ ID NO: 1, SEQ ID NO: 2, SEQ ID NO: 3, SEQ ID NO: 4, SEQ ID NO: 5, and SEQ ID NO: 8 and (ii) the amino acid sequence set forth in SEQ ID NO:7, wherein said encapsulating delivery vehicle comprises a therapeutic agent.

17. The tumor-targeted drug delivery composition of claim 1 comprising an NGR-containing molecule linked to a delivery vehicle, said NGR-containing molecule consists of 20, 25, 40, 50, 60, 70, 80, 90, or 100 contiguous amino acid residues.

18. The tumor-targeted drug delivery composition of claim 1, wherein said NGR-containing molecule is attached to the external surface of an encapsulating delivery vehicle.

19. The tumor-targeted drug delivery composition of claim 18, wherein said encapsulating delivery vehicle is a liposome and wherein said NGR-containing molecule is attached to the external surface of said liposome via a thiol to a maleimido moiety on the liposome.

20. The tumor-targeted drug delivery composition of claim 1, wherein said NGR-containing molecule comprises a cysteine residue at the carboxy terminus.

21. The tumor-targeted delivery composition of claim 1, wherein the NGR-containing molecule comprises the amino acid sequence of SEQ ID NO: 6.

22. The tumor-targeted delivery composition of claim 21, wherein the NGR-containing molecule consists of the amino acid sequence of SEQ ID NO: 6.

23. The tumor-targeted delivery composition of claim 16, wherein the NGR-containing molecule consists of the amino acid sequence of SEQ ID NO: 6.

24. The tumor-targeted delivery composition of claim 16, wherein the NGR-containing molecule is covalently attached to the encapsulating delivery vehicle.

25. The tumor-targeted drug delivery composition of claim 16, wherein the NGR-containing molecule is linked to the external surface of the encapsulating delivery vehicle.

* * * * *

UNITED STATES PATENT AND TRADEMARK OFFICE
CERTIFICATE OF CORRECTION

| | | |
|---|---|---|
| PATENT NO. | : 7,479,483 B2 | Page 1 of 8 |
| APPLICATION NO. | : 10/853895 | |
| DATED | : January 20, 2009 | |
| INVENTOR(S) | : Ponzoni et al. | |

It is certified that error appears in the above-identified patent and that said Letters Patent is hereby corrected as shown below:

Title Page; item (56);
    Under OTHER PUBLICATIONS, in Yvette et al., replace "doxorabicin" with
    --doxorubicin--.

Page 2, under OTHER PUBLICATIONS, in Huang X. et al., replace "targeteing" with --targeting--;

In Pastorino F. et al., replace "dissernination" with --dissemination--.

Column 3, Line 4, replace "0.5-2 folds" with --0.5-2 fold--;
    Line 4, replace "2-5 folds" with --2-5 fold--;
    Line 4, replace "5-10 folds" with --5-10 fold--;
    Line 5, replace "10-15 folds" with --10-15 fold--;
    Line 5, replace "15-20 folds" with --15-20 fold--;
    Line 5, replace "20-30 folds" with --20-30 fold--;
    Line 5, replace "30-40 folds" with --30-40 fold--;
    Line 29, replace "comprises" with --comprise--;
    Line 53, replace "0.5-2 folds" with --0.5-2 fold--;
    Line 53, replace "2-5 folds" with --2-5 fold--;
    Line 53, replace "5-10 folds" with --5-10 fold--;
    Line 53, replace "10-15 folds" with --10-15 fold--;
    Line 54, replace "15-20 folds" with --15-20 fold--;
    Line 54, replace "20-30 folds" with --20-30 fold--;
    Line 54, replace "30-40 folds" with --30-40 fold--;
    Line 61, replace "theraputic" with --therapeutic--.

Column 4, Line 31, replace "contiguous 80" with --80 contiguous--;
    Lines 31-32, replace "contiguous 90" with --90 contiguous--;
    Line 32, replace "contiguous 100" with --100 contiguous--;
    Line 33, replace "contiguous 125" with --125 contiguous--;

Signed and Sealed this
First Day of March, 2011

David J. Kappos
*Director of the United States Patent and Trademark Office*

Column 4, Line 34, replace "contiguous 175" with --175 contiguous--;
   Line 35, replace "contiguous 200" with --200 contiguous--;
   Line 36, replace "contiguous 350" with --350 contiguous--;
   Line 37, replace "NGR-containing" with --the NGR containing--;
   Line 52, replace "intracerebral, intracerebral" with --intracerebral--.

Column 5, Line 16, replace "bladder, flu-like symptoms" with --bladder,--;
   Lines 17-18, replace "dry mouth, loss of appetite, hair loss" with --dry mouth, hair loss--;
   Line 43, replace "and or" with --and/or--;
   Lines 48-49, replace "autoiimmune" with --autoimmune--;
   Line 63, replace "that are" with --that is--.

Column 6, Line 10, replace "contiguous 80" with --80 contiguous--;
   Line 11, replace "contiguous 90" with --90 contiguous--;
   Line 12, replace "contiguous 100" with --100 contiguous--;
   Lines 12-13, replace "contiguous 125" with --125 contiguous--;
   Line 14, replace "contiguous 175" with --175 contiguous--;
   Line 15, replace "contiguous 200" with --200 contiguous--;
   Line 15, replace "contiguous 350" with --350 contiguous--;
   Line 20, replace "24 hours" with --24 hour--.

Column 7, Line 8, replace "were" with --was--;
   Line 41, replace "ortbotopieally" with --orthotopically".

Column 8, Lines 25-26, replace "inventors" with --invention--;
   Line 31, replace "10-folds" with --10-fold--;
   Line 41, replace "comprises a" with --comprises--;
   Lines 43-44, replace "0.5-2 folds" with --0.5-2 fold--;
   Line 44, replace "2-5 folds" with --2-5 fold--;
   Line 44, replace "5-10 folds" with --5-10 fold--;
   Line 44, replace "15-20 folds" with --15-20 fold--;
   Line 44, replace "20-30 folds" with --20-30 fold--;
   Lines 44-45, replace "30-40 folds" with --30-40 fold--;
   Line 51, replace "effect" with --effect.--;
   Line 52, replace "cells" with --cell--.

Column 9, Line 4, replace "cells" with --cell--;
   Line 8, replace "derivatives" with --derivative--;
   Line 18, replace "comprise" with --comprises--;
   Line 26, replace "sphinomyelin" with --sphingomyelin--;
   Line 43, replace "molecule" with --molecules--.

CERTIFICATE OF CORRECTION (continued)
U.S. Pat. No. 7,479,483 B2

Column 10, Line 4, replace "an" with --a--;
    Lines 14-15, replace "derivatives" with --derivative--.

Column 11, Line 29, replace "add" with --acid--;
    Line 30, replace "as" with --amino acid--;
    Line 58, replace "Neuropilia-1" with --Neuropilin-1--;
    Line 60, replace "Neuropilitu-1" with --Neuropilin-1--.

Column 12, Line 5, replace "are" with --is--;
    Line 11, replace "which cell" with --which are cell--.

Column 13, Line 40, replace "cancer-gives" with --cancer gives--;
    Line 46, replace "have" with --has--;
    Line 62, replace "angiogeneeas" with --angiogenesis--.

Column 14, Lines 5-6, replace "eollagenease-1" with --collagenase-1--;
    Lines 52-53, replace "M-hydroxysuccinimide" with --N-hydroxysuccinimide--.

Column 15, Lines 41-42, replace "phosphalidylcholine" with --phsphatidylcholine--;
    Line 42, replace "phophatidylethanolaamine" with --phosphatidylethanolamine--;
    Line 63, replace "arc" with --are--.

Column 16, Line 48, replace "polyhydroxypropyloxaz line" with --polyhydroxypropyloxazoline--;
    Line 49, replace "polymehacrylamide" with --polymethacrylamide--;
    Line 49, replace "polyduuctbylacrylamid" with --polydimethylacrylamide,--.

Column 17, Line 14, replace "N-hydroxycthylammonium" with --N-hydroxyethylammonium--;
    Line 17, replace "trunethylanunonium" with --trimethylammonium--;
    Line 18, replace "carbamolyl" with --carbamoyl--;
    Line 22, replace "dioleoxylphosphatidyl" with --dioleoylphosphatidyl--;
    Line 37, replace "diphytanoylphosphatidylethanolaamine" with
    --diphytanoylphosphatidylethanolamine--;
    Line 46, replace "benzophorphrins" with --benzoporphyrin--;
    Line 53, replace "ifospfamide" with --ifosfamide--;
    Line 53, replace "ehlorambucil" with --chlorambucil--;
    Line 54, replace "chlormethhine" with --chlormethine--;
    Line 61, replace "tioguaninc" with --tioguanine--;
    Lines 63-64, replace "altetarmine" with --alretamine--.

Column 18, Line 2, replace "inotecan" with --irinotecan--;
    Line 22, replace "compound" with --compounds--;
    Line 28, replace "ctodolac" with --etodolac--;
    Line 29, replace "acetaminocin" with --acetominophen--;

CERTIFICATE OF CORRECTION (continued)
U.S. Pat. No. 7,479,483 B2

Column 18, Line 29, replace "suliudac" with --sulindac--;
        Line 30, replace "tiaprofenuie" with --tiaprofrenic--;
        Line 46, replace "tumistatin" with --tumstatin--;
        Line 47, replace "vasostalin" with --vasostatin--.

Column 20, Line 47, replace "liposomes," with --liposomes--.

Column 21, Line 45, replace "centrifugation" with --centrifugation.--;

Column 21, Line 64, replace "glucosoyl" with --glucosyl--.

Column 22, Line 6, replace "muein" with --murein--;
        Line 29, replace "agent" with --agents--;
        Line 39, replace "method" with --methods--;
        Lines 43-44, replace "0.5-2 folds" with --0.5-2 fold--;
        Line 44, replace "2-5 folds" with --2-5 fold--;
        Line 44, replace "5-10 folds" with --5-10 fold--;
        Line 44, replace "15-20 folds" with --15-20 fold--;
        Line 44, replace "20-30 folds" with --20-30 fold--;
        Lines 44-45, replace "30-40 folds" with --30-40 fold--;
        Line 45, replace "40-50 folds" with --40-50 fold--;
        Line 45, replace "50-100 folds" with --50-100 fold--;
        Line 54, replace "system" with --systems--.

Column 23, Line 51, replace "insipius" with --insipidus--;
        Line 64, replace "cytic" with --cystic--.

Column 24, Line 7, replace "pappillary" with --papillary--;
        Line 28, replace "uterer" with --ureter--;
        Line 37, replace "Berketts" with --Burkitt's--;
        Line 40, replace "orignin" with --origin--;
        Line 41, replace "rhabdomyoscarcoma" with --rhabdomyosarcoma--;
        Line 42, replace "tetratocarcinoma" with --teratocarcinoma--;
        Lines 45-46, replace "fibrosacoma" with --fibrosarcoma--;
        Line 46, replace "rhabdomyoscarama" with --rhabdomyosarcoma--;
        Line 47, replace "xenoderma pegmentosum" with --xeroderma pigmentosum--;
        Line 48, replace "keratoactanthoma" with --keratoacanthoma--;
        Line 57, replace "neoblastoma" with --neuroblastoma--.

Column 25, Line 26, replace "composition" with --compositions--;
        Lines 32-33, replace "composition" with --compositions--.

Column 27, Line 6, replace "composition" with --compositions--;
   Line 19, replace "sialastic" with --silastic--;
   Line 58, replace "ambomycin" with --albomycin--;
   Lines 61-62, replace "benzodepa" with --benzotepa--.

Column 28, Line 6, replace "eflonithine" with --eflornithine--.
   Line 3, replace "chlorlns" with --chlorins--;

Column 29, Line 12, replace "didenmin B" with --didemnin B--;
   Lines 30-31, replace "isohomohalicondrin B" with --isohomohalichondrin B--;
   Line 59, replace "ondansetron; ondansetron" with --odansetron--.

Column 31, Line 52, replace "that" with --of--;
   Line 63, replace "sodium" with --or sodium--.

Column 33, Line 1, replace "drug" with --the drug--;
   Line 38, replace "can" with --can be--.

Column 34, Line 5, replace "line" with --lines--;
   Line 6, replace "line" with --lines--;
   Line 7, replace "line" with --lines--;
   Line 18, replace "alleviate of one" with --alleviate one--;
   Line 29, replace "test to" with --the--;
   Line 61, replace "human" with --humans--.

Column 35, Line 42, replace "a" with --an--;
   Lines 61-62, replace "(Browder, supra); Klement, supra)"
   with --(Browder, supra; Klement, supra)--;
   Line 64, replace "for" with --or--.

Column 36, Line 18, replace "Si 5-8" with --S15-8--;
   Line 50, replace "DXR/gmol" with --DXR/µmol--.

Column 38, Line 47, replace "microvessels" with --microvessel--.

Column 39, Line 64, replace "pervious" with --previous--.

Column 40, Line 10, replace "neurblastoma" with --neuroblastoma--;
   Line 45, replace "requited" with --required--.

Column 43, Lines 8-9, replace "formulations" with --formulation--;
   Line 37, replace "recognize" with --recognizes--.

Column 44, Line 24, replace "delivery" with --deliver--.

CERTIFICATE OF CORRECTION (continued)
U.S. Pat. No. 7,479,483 B2

Please replace the Sequence Listing in the above-referenced
patent, from Column 43, Line 61 to Column 46, Line 59, with
the Sequence Listing provided below.

```
                    SEQUENCE LISTING

<160> NUMBER OF SEQ ID NOS: 8

<210> SEQ ID NO 1
 <211> LENGTH: 6
 <212> TYPE: PRT
 <213> ORGANISM: Homo sapiens

<400> SEQUENCE: 1

Asn Gly Arg Ala His Ala
 1               5

<210> SEQ ID NO 2
  <211> LENGTH: 5
  <212> TYPE: PRT
  <213> ORGANISM: Homo sapiens

<400> SEQUENCE: 2

Gly Asn Gly Arg Gly
  1               5

<210> SEQ ID NO 3
  <211> LENGTH: 5
  <212> TYPE: PRT
  <213> ORGANISM: Homo sapiens

<400> SEQUENCE: 3

Cys Asn Gly Arg Cys
  1               5
```

```
<210> SEQ ID NO 4
<211> LENGTH: 13
<212> TYPE: PRT
<213> ORGANISM: Homo sapiens

<400> SEQUENCE: 4

Cys Asn Gly Arg Cys Val Ser Gly Cys Ala Gly Arg Cys
1               5                   10

<210> SEQ ID NO 5
<211> LENGTH: 9
<212> TYPE: PRT
<213> ORGANISM: Homo sapiens

<400> SEQUENCE: 5

Cys Val Leu Asn Gly Arg Met Glu Cys
1               5

<210> SEQ ID NO 6
<211> LENGTH: 19
<212> TYPE: PRT
<213> ORGANISM: Homo sapiens

<400> SEQUENCE: 6

Gly Asn Gly Arg Gly Gly Val Arg Ser Ser Arg Thr Pro Ser Asp
1               5                   10                  15

Lys Tyr Cys

<210> SEQ ID NO 7
<211> LENGTH: 10
<212> TYPE: PRT
<213> ORGANISM: Homo sapiens

<400> SEQUENCE: 7

Val Arg Ser Ser Ser Arg Thr Pro Ser Asp
1               5                   10
```

CERTIFICATE OF CORRECTION (continued)
U.S. Pat. No. 7,479,483 B2

```
<210> SEQ ID NO 8
<211> LENGTH: 6
<212> TYPE: PRT
<213> ORGANISM: Homo sapiens

<400> SEQUENCE: 8

Gly Asn Gly Arg Gly Gly
1               5
```

UNITED STATES PATENT AND TRADEMARK OFFICE
CERTIFICATE OF CORRECTION

PATENT NO.        : 7,479,483 B2
APPLICATION NO.   : 10/853895
DATED             : January 20, 2009
INVENTOR(S)       : Ponzoni et al.

Page 1 of 1

It is certified that error appears in the above-identified patent and that said Letters Patent is hereby corrected as shown below:

Title Page, under Item (73) (Assignees), replace "Monte (IT)"
with --Monte Tabor (IT)--;

Under Item (73) (Assignees), replace "University of Alberta"
with --The Governors of the University of Alberta--;

Signed and Sealed this
Twenty-eighth Day of June, 2011

David J. Kappos
*Director of the United States Patent and Trademark Office*